US012773210B2

(12) United States Patent
Kawayoke et al.

(10) Patent No.: US 12,773,210 B2
(45) Date of Patent: Oct. 27, 2026

(54) CLIP DEVICE

(71) Applicant: OLYMPUS MEDICAL SYSTEMS CORP., Tokyo (JP)

(72) Inventors: Shoichiro Kawayoke, Hino (JP); Masaru Yuasa, Hachioji (JP); Jun Yako, Hino (JP); Shinichi Jida, Hachioji (JP); Shotaro Yoshinaga, Machida (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 85 days.

(21) Appl. No.: 18/902,562

(22) Filed: Sep. 30, 2024

(65) Prior Publication Data

US 2026/0090804 A1 Apr. 2, 2026

(51) Int. Cl.
*A61B 17/08* (2006.01)
*A61B 17/00* (2006.01)

(52) U.S. Cl.
CPC ...... *A61B 17/083* (2013.01); *A61B 17/00234* (2013.01); *A61B 2017/00296* (2013.01); *A61B 2017/00367* (2013.01); *A61B 2017/00862* (2013.01)

(58) Field of Classification Search
CPC . A61B 17/00234; A61B 17/083; A61B 17/08; A61B 17/10; A61B 2017/00862; A61B 2017/00367; A61B 2017/00296
USPC ................ 606/155, 153, 151, 157, 143, 142
See application file for complete search history.

(56) References Cited

U.S. PATENT DOCUMENTS

| | | | | |
|---|---|---|---|---|
| 2007/0112359 A1* | 5/2007 | Kimura .............. | A61B 17/1222 606/142 |
| 2009/0275959 A1* | 11/2009 | Cui .................... | A61B 17/1285 606/143 |
| 2017/0086824 A1* | 3/2017 | Khan ................... | A61B 17/068 |
| 2018/0333156 A1* | 11/2018 | Hayashi ............. | A61B 17/1285 |
| 2022/0378431 A1* | 12/2022 | Reydel ............... | A61B 17/1227 |

* cited by examiner

*Primary Examiner* — Jocelin C Tanner
(74) *Attorney, Agent, or Firm* — Schwegman Lundberg & Woessner, P.A.

(57) ABSTRACT

A clip device includes: a clip which has an arm configured to be openable and closable in an opening and closing direction; and a holder which supports the clip and extends in a first longitudinal direction along a first longitudinal axis, wherein the arm is configured to pivot about a proximal end portion of the arm relative to the holder in an insertion form in which the arm is closed to be insertable through a channel of an endoscope.

20 Claims, 35 Drawing Sheets

CLIP DEVICE

BACKGROUND OF THE INVENTION

Field of the Invention

The present invention relates to a clip device.

Description of Related Art

In endoscopic treatment, medical devices such as clip devices for treating biological tissue are used. These medical devices are introduced to the treatment site by an applicator (introducing device) that can be inserted through a treatment tool insertion channel of an endoscope.

Patent Document 1 describes a clip device for treating biological tissue. The clip device described in Patent Document 1 is provided with a clip arm, and the clip device is configured to be insertable through a treatment tool insertion channel of an endoscope.

PATENT DOCUMENTS

[Patent Document 1] U.S. Patent Application Publication No. 2022/0378431

SUMMARY OF THE INVENTION

However, when the clip device is inserted into the treatment tool insertion channel of the endoscope, the clip arm may come into contact with the treatment tool insertion channel, thereby reducing the insertability of the clip device.

In consideration of the above circumstances, an object of the present invention is to provide a clip device that has good insertability when inserted into a treatment tool insertion channel or the like of an endoscope.

In order to solve the above problems, the present invention proposes the following means.

A clip device according to a first aspect of the present invention includes: a clip which has an arm configured to be openable and closable in an opening and closing direction; and a holder which supports the clip and extends in a first longitudinal direction along a first longitudinal axis, wherein the arm is configured to pivot about a proximal end portion of the arm relative to the holder in an insertion form in which the arm is closed to be insertable through a channel of an endoscope.

The clip device of the present invention has good insertability when inserted into the treatment tool insertion channel or the like of the endoscope and allows a user to begin treatment of biological tissue as soon as possible.

DETAILED DESCRIPTION OF THE INVENTION

Figure 1:
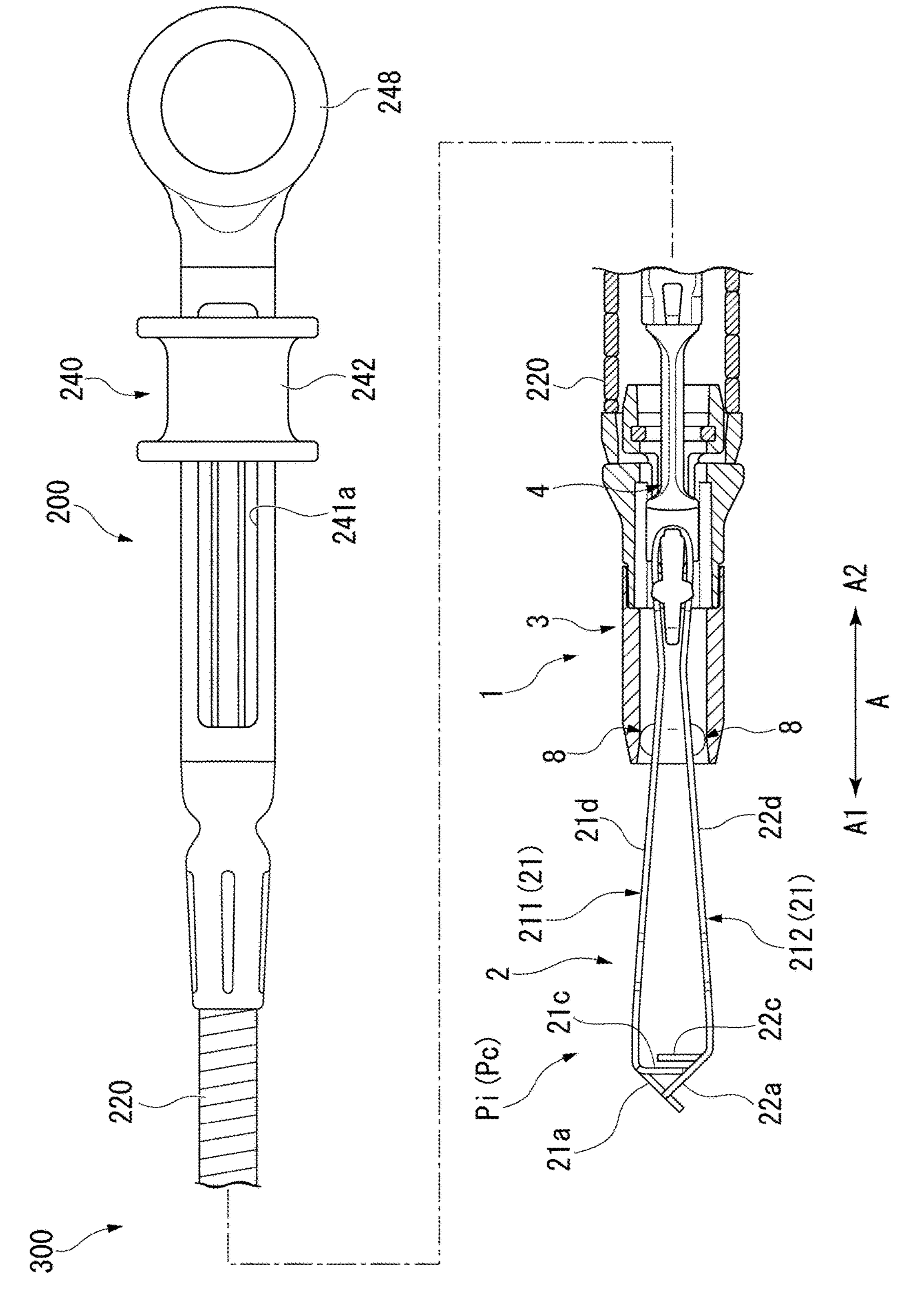
FIG. 1 is a side view showing a clip device.

Hereinafter, a clip device according to an embodiment will be described with reference to the drawings. In the following description, components having the same or similar functions are denoted by the same reference numerals. In addition, duplicate descriptions of those components may be omitted.

First Embodiment

[Clip Device 300]

A clip device 300 according to a first embodiment of the present invention will be described with reference to FIGS. 1 to 30.

FIG. 1 is a side view showing the clip device 300.

The clip device 300 includes a clip introducing device (applicator) 200 and a clip unit 1. The clip unit 1 is loaded into the clip introducing device 200.

[Clip Introducing Device 200]

Figure 2:
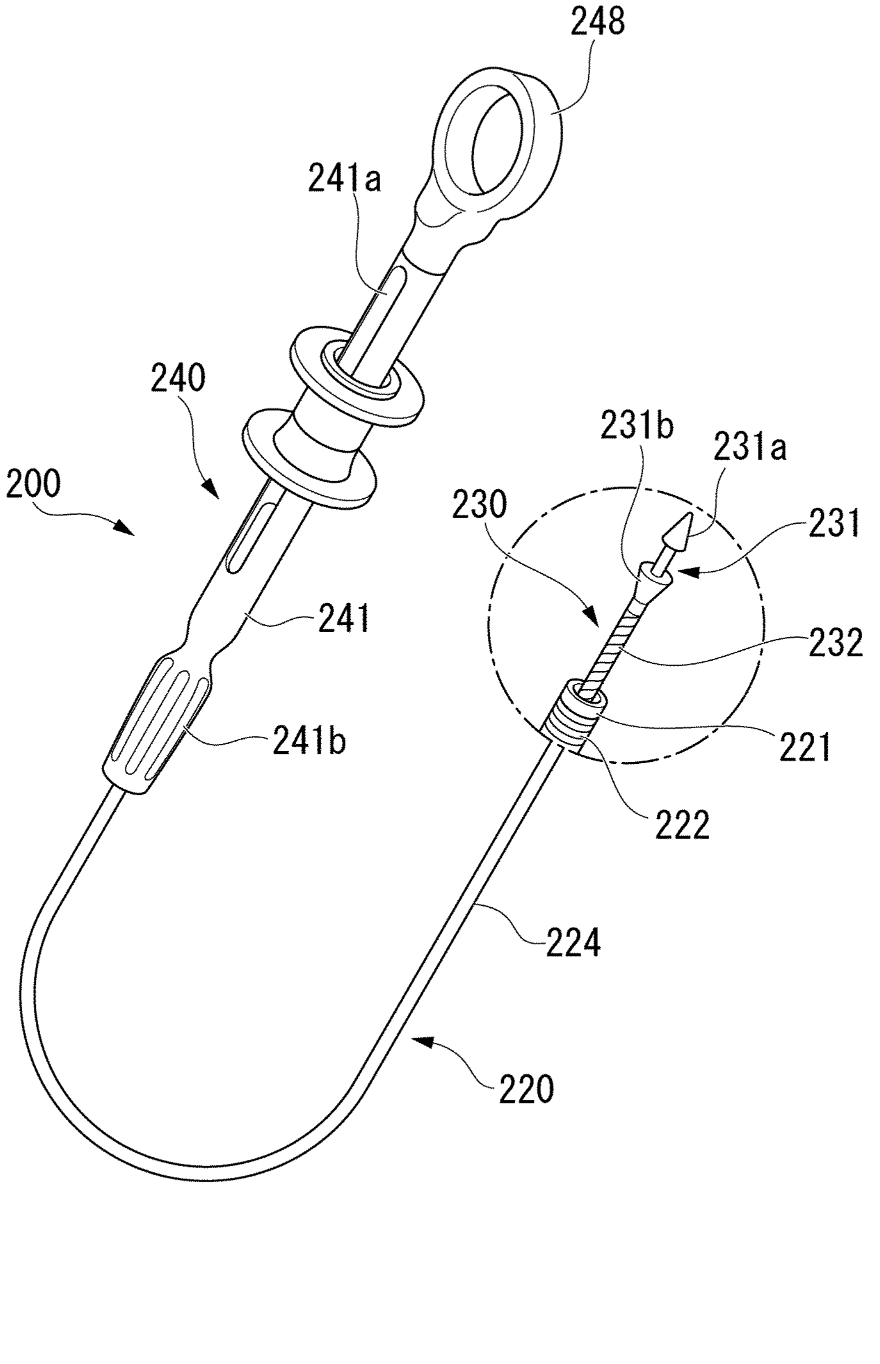
FIG. 2 is a perspective view showing a clip introducing device.

FIG. 2 is a perspective view showing the clip introducing device 200.

As shown in FIG. 2, the clip introducing device (applicator) 200 includes a sheath 220, an operating wire 230, and an operation unit 240. The clip introducing device 200 is inserted, for example, through a treatment tool insertion channel (channel) N of an endoscope and used in combination with the endoscope (see FIGS. 29 and 30). Therefore, the sheath 220 is formed to be sufficiently longer than the length of the treatment tool insertion channel N of the endoscope. The sheath 220 is flexible and bends in accordance with the curvature of the insertion portion of the endoscope.

As shown in FIG. 2, the sheath 220 has a distal tip 221, a distal coil 222, and a hand side coil 224, and is formed into an elongated tubular shape as a whole. The distal coil 222 is disposed on the distal end portion side of the sheath 220. The distal tip 221 is disposed at the distal end portion of the distal coil 222.

As shown in FIG. 2, the operating wire (power transmission portion) 230 has an arrowhead hook (connecting portion) 231 connected to the clip unit 1, and a wire 232 for operating the arrowhead hook 231.

As shown in FIG. 2, the arrowhead hook 231 has a substantially conical engagement portion 231*a* that engages with the clip unit 1, and a wire connecting portion 231*b* that is provided at the proximal end of the engagement portion 231*a*. The arrowhead hook 231 is made of a metal material such as stainless steel.

The wire 232 is inserted through the sheath 220 so as to be freely movable forward and backward. The distal end portion of the wire 232 is fixed to the proximal end of the wire connecting portion 231*b* by, for example, welding.

As shown in FIG. 2, the operation unit 240 has an operation unit body 241, a slider 242, and a thumb ring 248. The operation unit body 241, the slider 242, and the thumb ring 248 are formed by injection molding using, for example, a resin material. The operation unit body 241 has a slit portion 241*a* and a rotating grip 241*b* at the distal end side. The slit portion 241*a* supports the slider 242 so that the slider 242 is movable forward and backward.

The slider 242 is attached so as to be movable forward and backward in the longitudinal direction of the operation unit body 241, and the proximal end of the wire 232 is attached to the slider 242. As the slider 242 moves forward and backward along the operation unit body 241, the wire 232 moves forward and backward relative to the sheath 220, and the arrowhead hook 231 moves forward and backward.

The thumb ring 248 is attached to the proximal end of the operation unit body 241 so as to be rotatable around the longitudinal axis of the operation unit body 241.

[Clip Unit 1]

Figure 3:
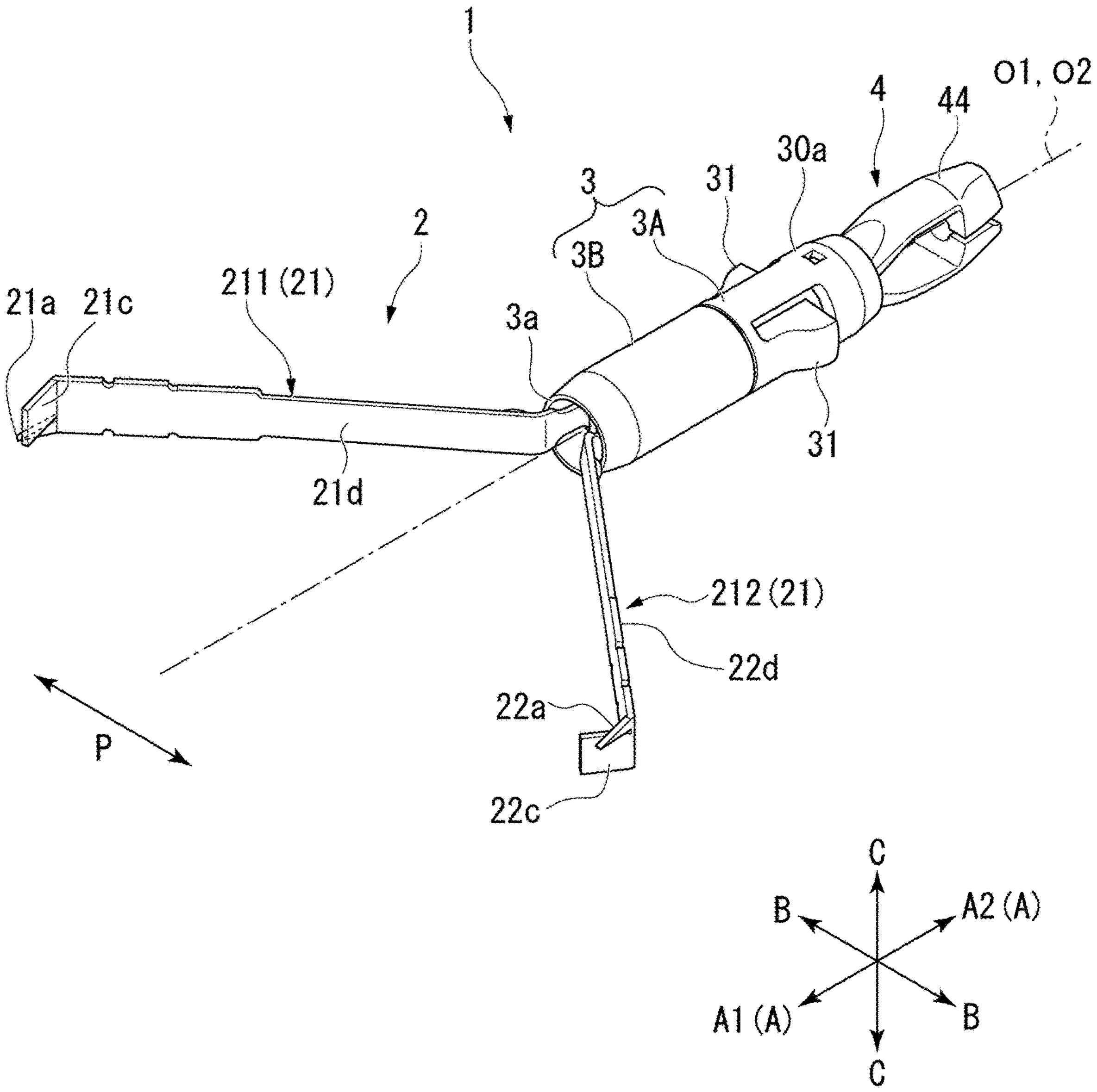
FIG. 3 is a perspective view showing a clip unit.
Figure 4:
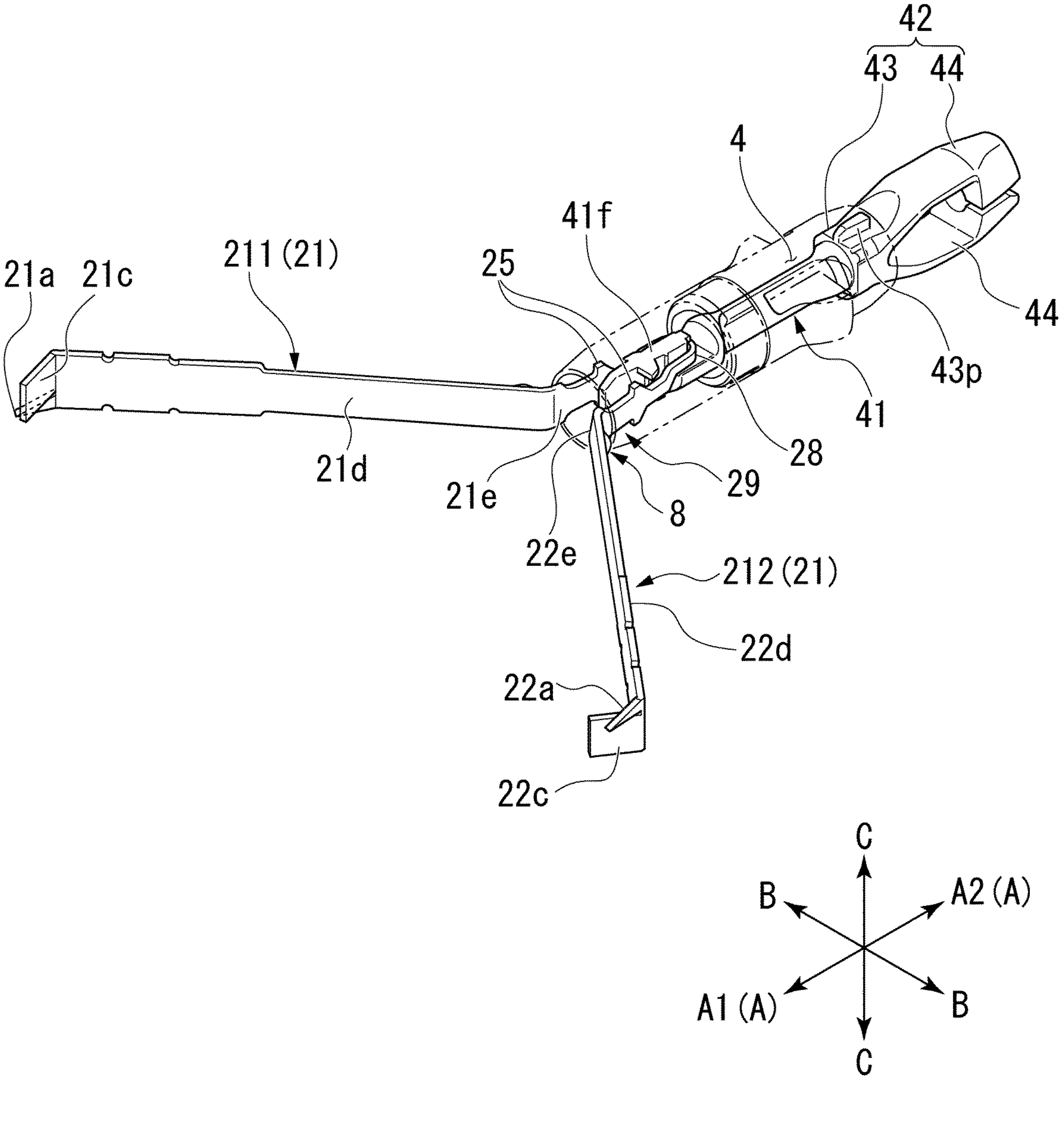
FIG. 4 is a perspective view showing the clip unit with a pressing tube being transparent.

FIG. 3 is a perspective view showing the clip unit 1. FIG. 4 is a perspective view showing the clip unit 1 with a pressing tube 3A being transparent.

As shown in FIG. 3, the clip unit 1 has a clip 2, a pressing member (holder) 3, and a connecting member 4.

In the following description, the side of the clip 2 in the longitudinal direction (first longitudinal direction) A of the clip unit 1 is referred to as the distal end side (distal side) A1 of the clip unit 1, and the side of the connecting member 4 is referred to as the proximal end side (proximal side) A2 of the clip unit 1. Further, the direction perpendicular to the longitudinal direction A is referred to as the "first direction B" or the "left and right direction B." Further, the direction perpendicular to the longitudinal direction A and the first direction B is referred to as the "second direction C" or the "up and down direction C".

Figure 5:
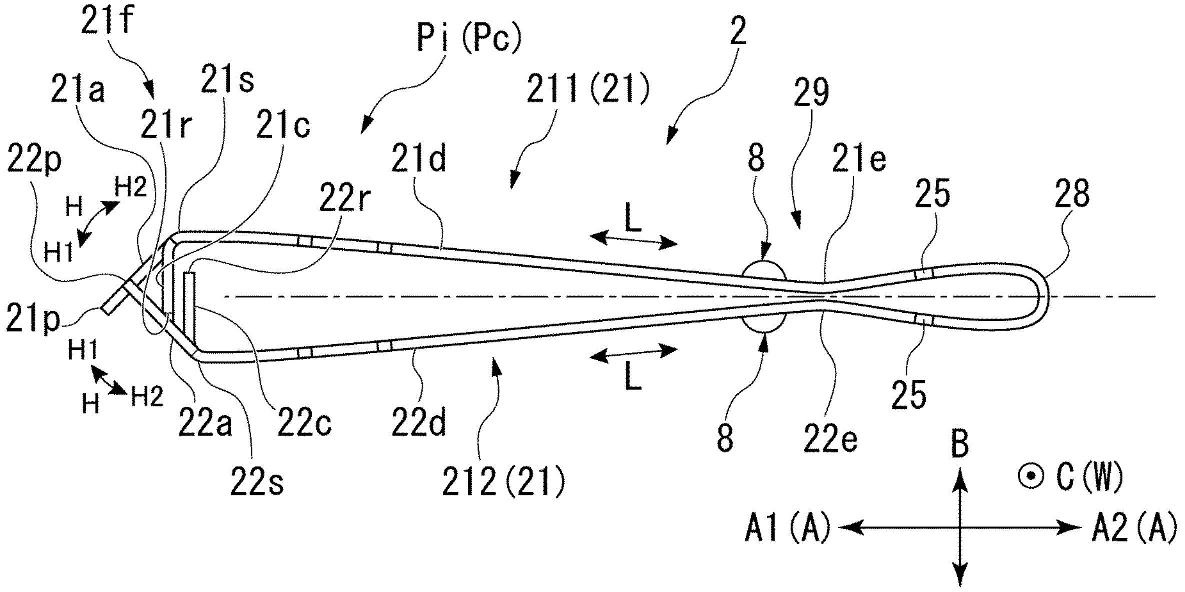
FIG. 5 is a side view showing a clip in a closed form.
Figure 6:
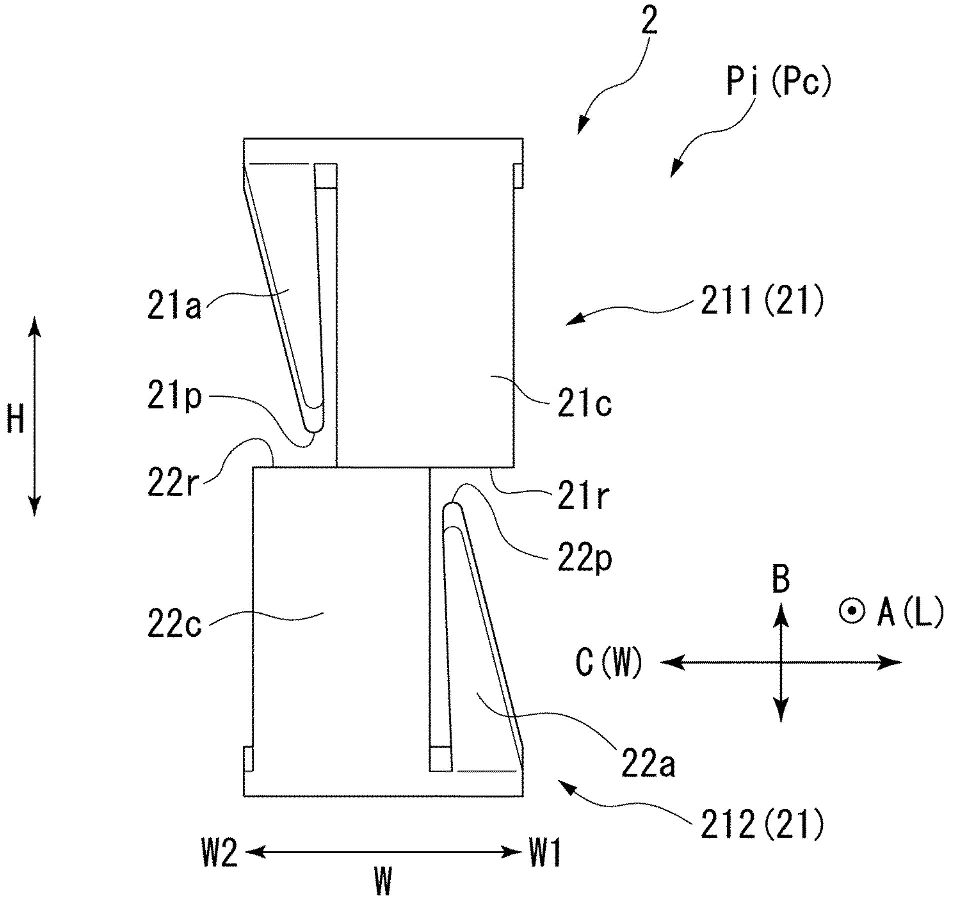
FIG. 6 is a front view showing the clip in a closed form.

FIG. 5 is a side view showing the clip 2 in a closed form Pc. FIG. 6 is a front view showing the clip 2 in a closed form Pc.

The clip 2 is formed by bending a metal plate at the center. The clip 2 has a pair of arms 21 that are openable and closable toward the distal end side A1, and a connecting portion 28 that connects the pair of arms 21. An engagement portion 25 is provided at a proximal end portion 29 of the arm 21. The proximal end side A2 of the clip 2 is inserted into an internal space 38 of a pressing member 3.

Figure 7:
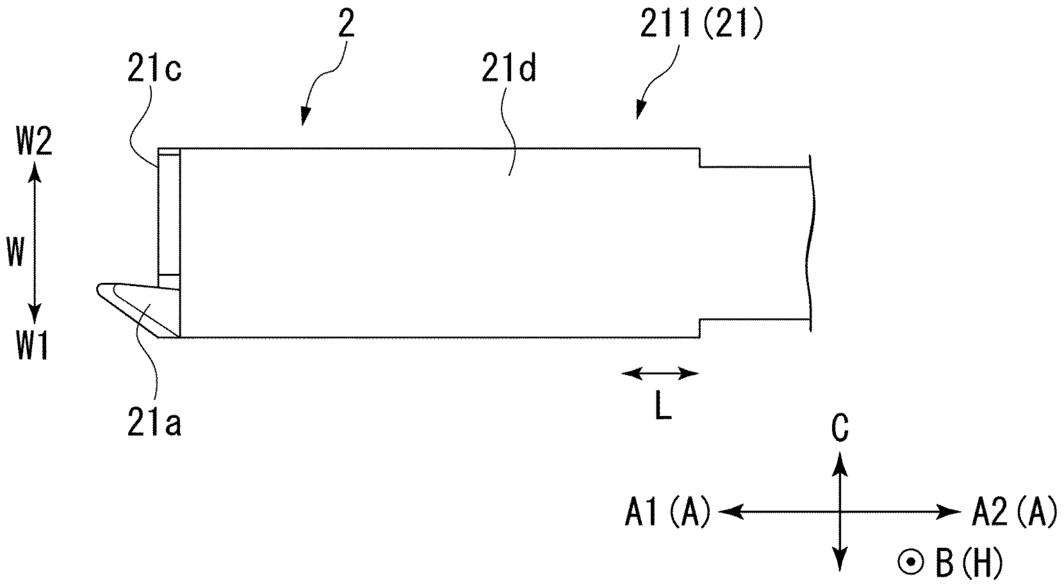
FIG. 7 is a side view showing a first arm when viewed from the inside.
Figure 8:
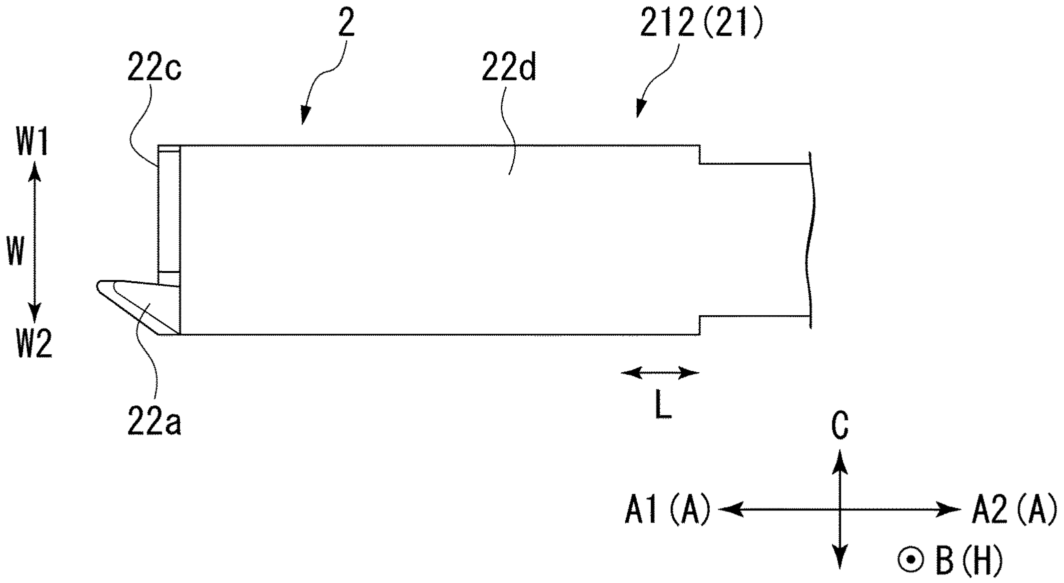
FIG. 8 is a side view showing a second arm when viewed from the inside.

FIG. 7 is a side view showing a first arm 211 when viewed from the inside. FIG. 8 is a side view showing a second arm 212 when viewed from the inside.

The pair of arms 21 have the first arm 211 and the second arm 212 that are openable and closable in an opening and closing direction H. The pair of arms 21 can transition between an open form Po (open state) and a closed form Pc (closed state). The first arm 211 and the second arm 212 are arranged on both sides of a central axis O1 in the longitudinal direction A of the clip unit 1. Furthermore, the clip 2 may have three or more arms.

In the opening and closing direction H, the direction in which one arm approaches the other arm is referred to as the "closing side H1." In the opening and closing direction H, the direction in which one arm moves away from the other arm is referred to as the "opening side H2." The direction in which the pair of arms 21 face each other is referred to as the "inside", and the side opposite the inside is referred to as the "outside".

The first arm 211 has a first anchor (anchor) 21*a*, first claw (claw) 21*c*, and a first arm body (arm body) 21*d*. Furthermore, the first arm 211 may not have the first anchor 21*a*.

The second arm 212 has a second anchor 22*a*, a second claw 22*c*, and a second arm body 22*d*. Furthermore, the second arm 212 may not have the second anchor 22*a*. Since the second arm 212 has a shape similar to that of the first arm 211, only the differences will be described below.

The first arm body 21*d* is formed in a flat plate shape extending in a longitudinal direction (second longitudinal direction) L along the longitudinal axis (second longitudinal axis). The first arm body 21*d* is a portion that mainly grasps tissue. A direction perpendicular to the longitudinal direction L and the opening and closing direction H is referred to as a "width direction W."

The first claw 21*c* is provided at a distal end (distal end portion) 21*s* of the first arm body 21*d* and extends toward the closing side H1 in the opening and closing direction H. The first claw 21*c* extends from the first anchor 21*a* toward the closing side H1 in the opening and closing direction H. The first claw 21*c* is formed by, for example, hollowing out.

The first anchor 21*a* is provided at the distal end 21*s* of the first arm body 21*d* and extends toward the closing side H1 in the opening and closing direction H. The first anchor 21*a* is disposed on one side W1 in the width direction W. The distal end 21*p* of the first anchor 21*a* is formed into a sharp tapered shape so as to easily puncture the mucosa. The first anchor 21*a* is formed in a substantially right-angled triangular shape when viewed from the longitudinal direction L. The first anchor 21*a* extends inward in the width direction W, and the distal end 21*p* is unlikely to come into contact with the treatment tool insertion channel N of the endoscope.

The first anchor 21*a* is disposed on the opening side H2 in the opening and closing direction H in relation to the first claw 21*c*. The first claw 21*c* and the first anchor 21*a* extend from the same portion (distal end 21*s*) when viewed from the width direction W. Furthermore, the first claw 21*c* and the first anchor 21*a* may not extend from the same portion when viewed from the width direction W. At least the distal end 21*p* of the first anchor 21*a* may be disposed on the opening side H2 in the opening and closing direction H in relation to the first claw 21*c*. The first anchor 21*a* is formed, for example, by bending the distal end of the first arm 211.

When the clip 2 is in the open form Po, it is desirable that the distal end 21*p* of the first anchor 21*a* be disposed on the distal end side A1 in relation to a distal end 21*r* of the first claw 21*c*. This is because when the clip 2 in the open form Po approaches tissue from the front, the distal end 21*p* of the first anchor 21*a* comes into contact with the tissue first.

When the clip 2 is in the closed form Pc, the first claw 21*c* and the second claw 22*c* overlap when viewed from the longitudinal direction L, and the first claw 21*c* is disposed on the distal end side A1 in relation to the second claw 22*c*.

The first anchor 21*a* is disposed on one side W1 in the width direction W. The second anchor 22*a* is disposed on the other side W2 in the width direction W. When the clip 2 is in the closed form Pc, the first anchor 21*a* and the second anchor 22*a* do not overlap but are spaced apart when viewed from the longitudinal direction L, and are arranged rotationally symmetrical relative to the central axis O2 in the longitudinal direction A of the clip 2.

The first arm body 21*d* has a flat plate-shaped gripping portion 21*f* and a first sliding portion (curved portion) 21*e*. The second arm body 22*d* has a flat plate-shaped gripping portion 22*f* and a second sliding portion (curved portion) 22*e*.

The first sliding portion 21*e* is a portion that elastically deforms when the first arm 211 is pulled into the pressing member 3. The distal end of the first sliding portion 21*e* is connected to the first arm body 21*d*. The proximal end of the first sliding portion 21*e* is connected to the connecting portion 28.

As shown in FIG. 4, the engagement portion 25 is a member that can be engaged with a fastening member 32 of the pressing member 3. The distal end side A1 of the engagement portion 25 is formed as a slope having an obtuse angle relative to the longitudinal direction A, and the proximal end side A2 is formed as a slope having an acute angle relative to the longitudinal direction A.

The connecting portion 28 connects the first arm 211 and the second arm 212. The first arm 211 and the second arm 212 connected by the connecting portion 28 are provided so as to be able to open and close toward the distal end side A1. The connecting portion 28 is bent into a U-shape and is connected to a hook 41*f* of the connecting member 4. The connecting portion 28 is biased so that the pair of arms 21 are in the open form Po. Therefore, the pair of arms 21 of the clip 2 have a self-expanding force in the opening and closing direction H.

The connecting portion 28 and the hook 41*f* of the connecting member 4 are connected by inserting the hook 41*f* of the connecting member 4 into the connecting portion 28 which is formed in a U-shape. When the connecting portion 28 is connected to the connecting member 4, the opening and closing direction H of the pair of arms 21 substantially coincides with the left and right direction B.

Figure 9:
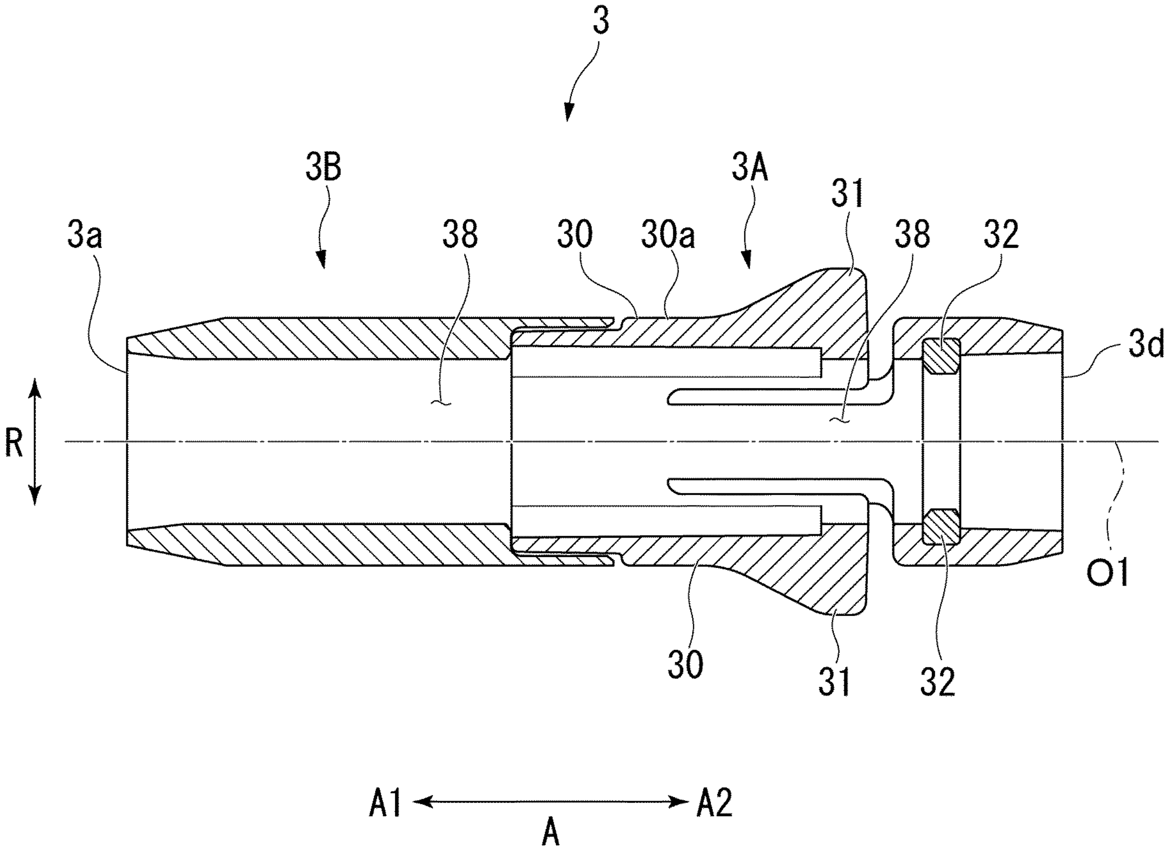
FIG. 9 is a cross-sectional view of a pressing member in a longitudinal direction.

FIG. 9 is a cross-sectional view of the pressing member 3 in the longitudinal direction A.

The pressing member (tubular member) 3 is a cylindrical member capable of accommodating at least a part of the clip 2. The pressing member 3 is a member extending in the longitudinal direction A along the longitudinal axis (first longitudinal axis). The pressing member 3 has the internal space 38 through which the clip 2 moves forward and backward in the longitudinal direction A. The pressing member 3 can fix the clip 2, which is pulled into the internal space 38, in a closed state. As shown in FIG. 5, the pressing member 3 has a pressing tube 3A provided on the proximal end side A2 and a pressing pipe 3B provided on the distal end side A1.

Figure 10:
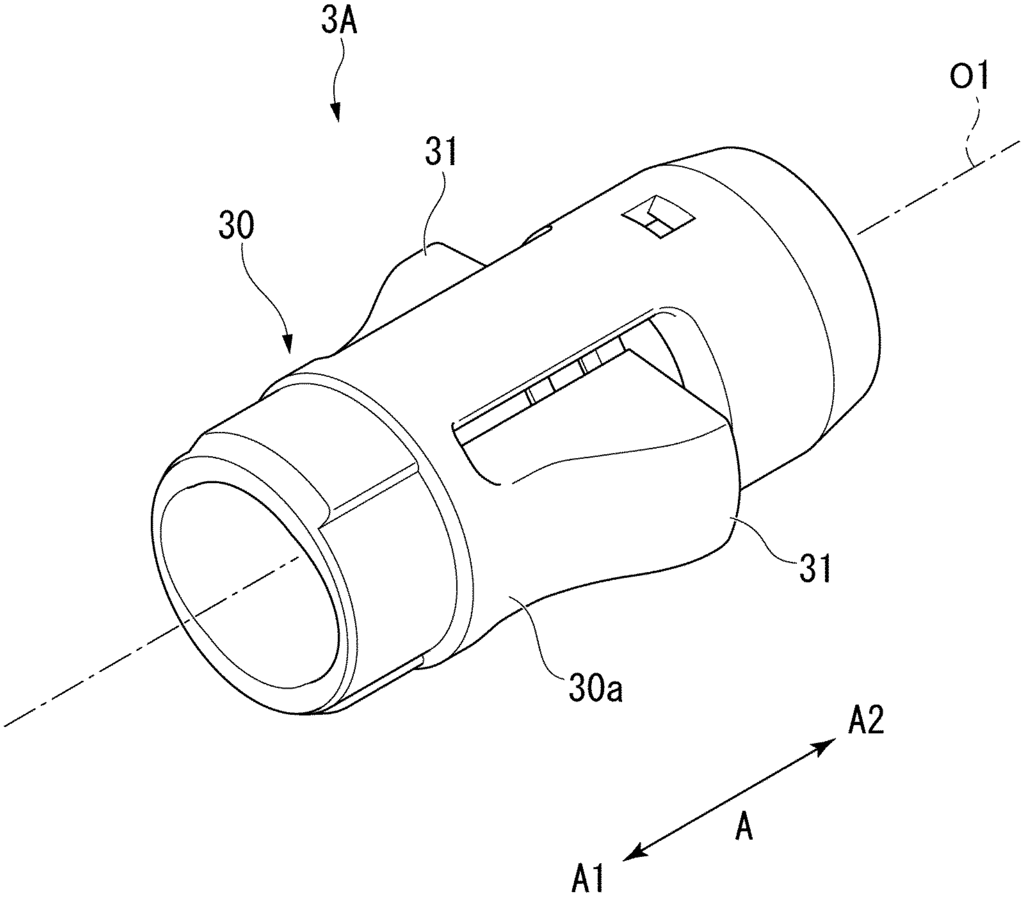
FIG. 10 is a perspective view of the pressing tube.

FIG. 10 is a perspective view of the pressing tube 3A.

As shown in FIG. 10, the pressing tube (second tubular member) 3A has a pressing tube body 30 formed in a cylindrical shape, a protruding/retracting wing 31, and the fastening member 32.

The pressing tube body 30 is formed by injection molding a material softer than the clip 2, for example, a thermoplastic resin having a suitable elasticity, such as PPA (polyphthalamide), PA (polyamide), PEEK (polyether ether ketone), and LCP (liquid crystal polymer). Furthermore, the pressing tube body 30 may be made of a metal instead of a thermoplastic resin.

Figure 11:
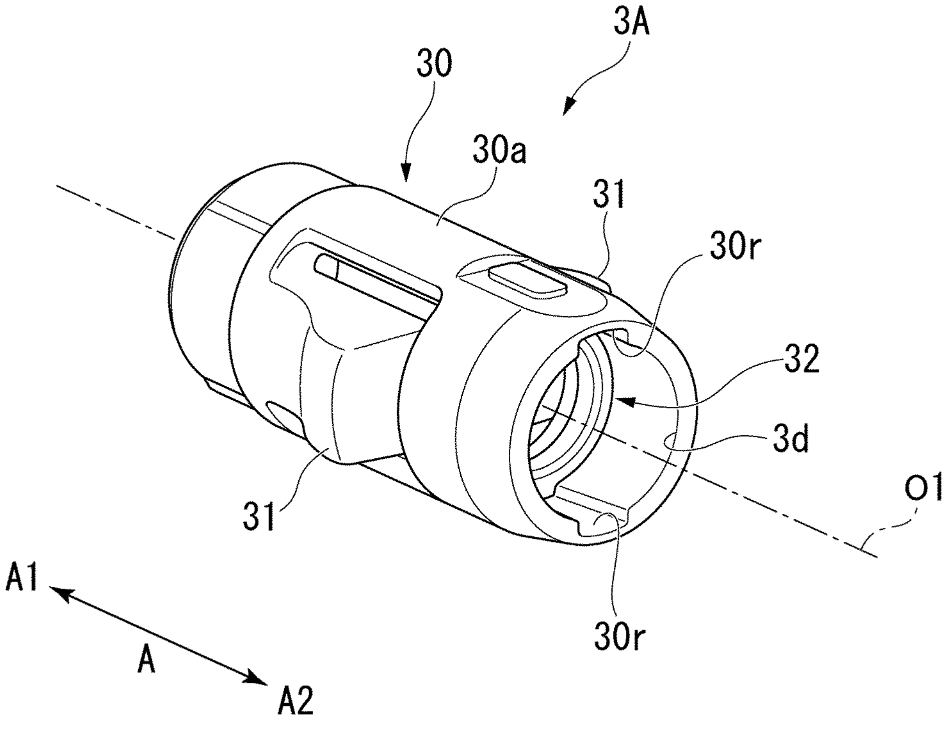
FIG. 11 is a perspective view of the pressing tube when viewed from a proximal end side.

FIG. 11 is a perspective view of the pressing tube 3A when viewed from the proximal end side A2.

An engagement recess 30*r* that engages with an engagement protrusion 43*p* of the connecting member 4, which will be described later, is formed in a proximal end opening 3*d* of the pressing tube body 30. The engagement recesses 30*r* are provided on both sides of the central axis O1.

The protruding/retracting wings 31 are a pair of convex portions that protrude and retract relative to an outer peripheral surface 30*a* of the pressing tube body 30. The protruding/retracting wings 31 are provided on both sides of the central axis O1. The protruding/retracting wings 31 have a basic orientation of protruding state in which they protrude outward in the radial direction R relative to the outer peripheral surface 30*a*. The protruding/retracting wing 31 receives a force directed from the outside to the inside in the radial direction R, so that the protruding/retracting wing 31 is retracted into the outer peripheral surface 30*a* to become the retracted state. When the above force is released, the protruding/retracting wing 31 returns from the retracted state to the protruding state.

The fastening member 32 is a ring-shaped member provided in the internal space 38 of the pressing tube 3A. The fastening member 32 is made of metal. Furthermore, the fastening member 32 only needs to be formed so as to be harder than the pressing tube body 30, and may be made, for example, of a thermoplastic resin instead of metal.

The pressing pipe (first tubular member) 3B is a metallic cylindrical member. The pressing pipe 3B is press-fitted into the distal end portion of the pressing tube 3A. The pressing tube 3A and the pressing pipe 3B may be connected by thermal welding, adhesion, or screw fastening.

Figure 12:
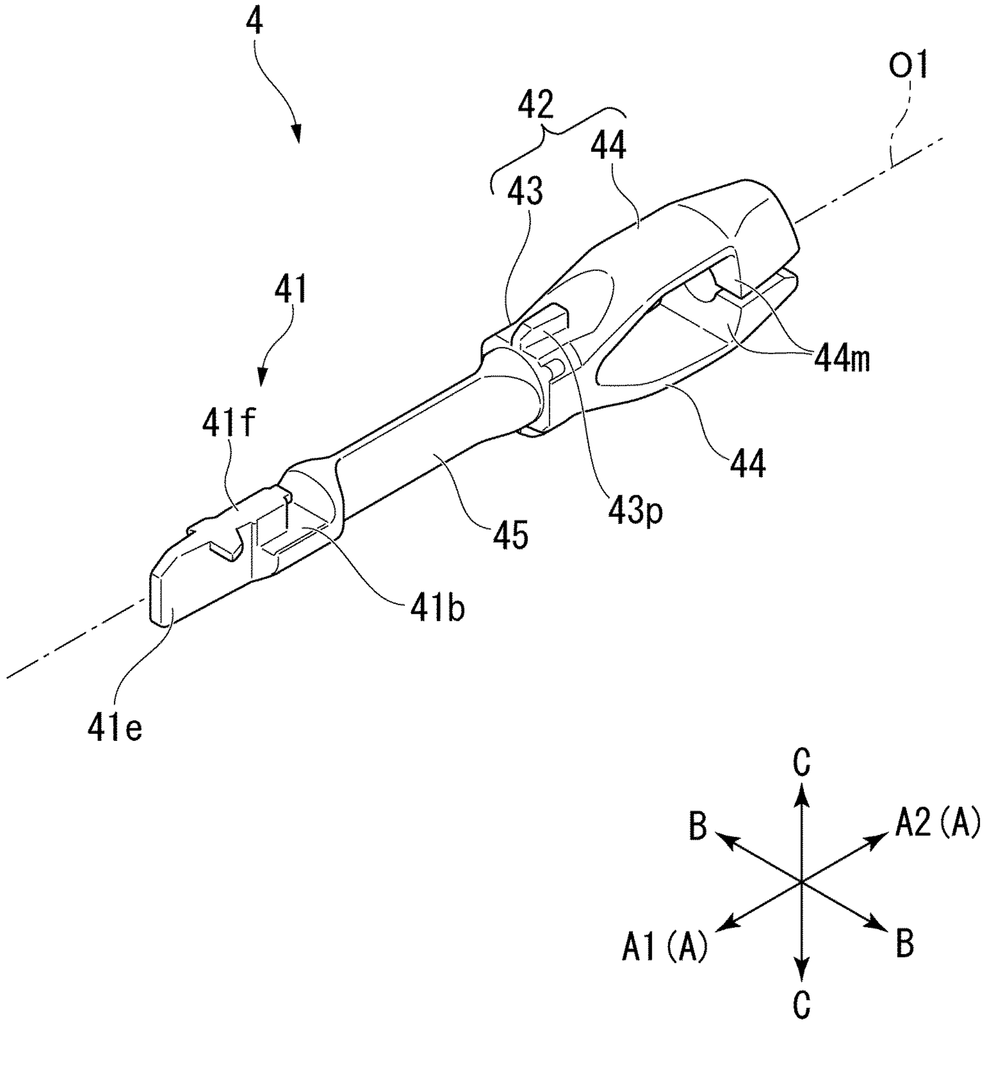
FIG. 12 is a perspective view of a connecting member.

FIG. 12 is a perspective view of the connecting member 4.

The connecting member 4 is detachably connected to the connecting portion 28 of the clip 2. Further, the connecting member 4 is detachably connected to the arrowhead hook 231 that passes through the inside of the sheath 220. That is, the connecting member 4 connects the clip 2 to the arrowhead hook 231. As shown in FIG. 12, the connecting member 4 has a distal end connecting portion 41 provided at the distal end, a proximal end connecting portion 42 provided at the proximal end, and a rod-shaped portion 45 connecting the distal end connecting portion 41 to the proximal end connecting portion 42.

As shown in FIG. 12, the distal end connecting portion 41 has the hook 41*f* at the distal end, a breakable portion 41*b* provided on the proximal end side A2 of the hook 41*f*, and a distal end expanding portion 41*e*. The distal end connecting portion 41 can be inserted through the internal space 38 of the pressing member 3 when connected to the clip 2.

The hook 41*f* extends in the up and down direction C perpendicular to the central axis O1, and is formed in a generally columnar rod shape. The hook 41*f* extends from the "lower side" to the "upper side" in the up and down direction C. The connecting portion 28 of the clip 2 is hooked from above onto the hook 41*f*.

The breakable portion 41*b* breaks when a breaking force is applied to the hook 41*f* by pulling the connecting portion 28 toward the proximal end side A2. Furthermore, the breakable portion 41*b* may have a mechanism for releasing the connection between the connecting portion 28 of the clip 2 and the hook 41*f* of the connecting member 4. For example, the breakable portion 41*b* may be a mechanism that releases the connection between the connecting portion 28 and the hook 41*f* by deforming (plastic deformation or elastic deformation) without breaking.

The proximal end connecting portion 42 is an engagement portion with which the arrowhead hook 231 of the clip introducing device 200 is engaged (connected). As shown in FIG. 12, the proximal end connecting portion 42 has a connecting portion body 43 and a connecting arm 44.

The connecting portion body 43 is provided at the proximal end of the rod-shaped portion 45. An engagement convex portion 43*p* which protrudes in the up and down direction C is formed in the connecting portion body 43. When the engagement convex portion 43*p* engages with an engagement concave portion 30*r* provided in the proximal end opening of the pressing member 3, the relative rotation between the pressing member 3 and the connecting member 4 in the circumferential direction relative to the longitudinal direction A is restricted.

The connecting arm (a pair of legs) 44 is provided at the proximal end of the connecting portion body 43 and is bifurcated. The connecting arm 44 is elastically deformable in the up and down direction C relative to the connecting portion body 43 and is openable and closable relative to the connecting portion body 43. The connecting arm 44 is provided with a notch 44*m* for grasping and accommodating the engagement portion 231*a* of the arrowhead hook 231. The notch 44*m* is formed in a shape that closely contacts the outer peripheral surface of the engagement portion 231*a* of the arrowhead hook 231. The connecting arm 44 is connectable to the arrowhead hook 231 of the clip introducing device 200 in the open form Po, and can maintain the connection with the arrowhead hook 231 of the clip introducing device 200 in the closed form Pc.

The rod-shaped portion 45 is a substantially rod-shaped member extending in the longitudinal direction A. The rod-shaped portion 45 is provided between the distal end connecting portion 41 and the proximal end connecting portion 42 and connects the distal end connecting portion 41 to the proximal end connecting portion 42. The rod-shaped portion 45 is insertable through the internal space 38 of the pressing member 3.

[Cartridge 5]

Figure 13:
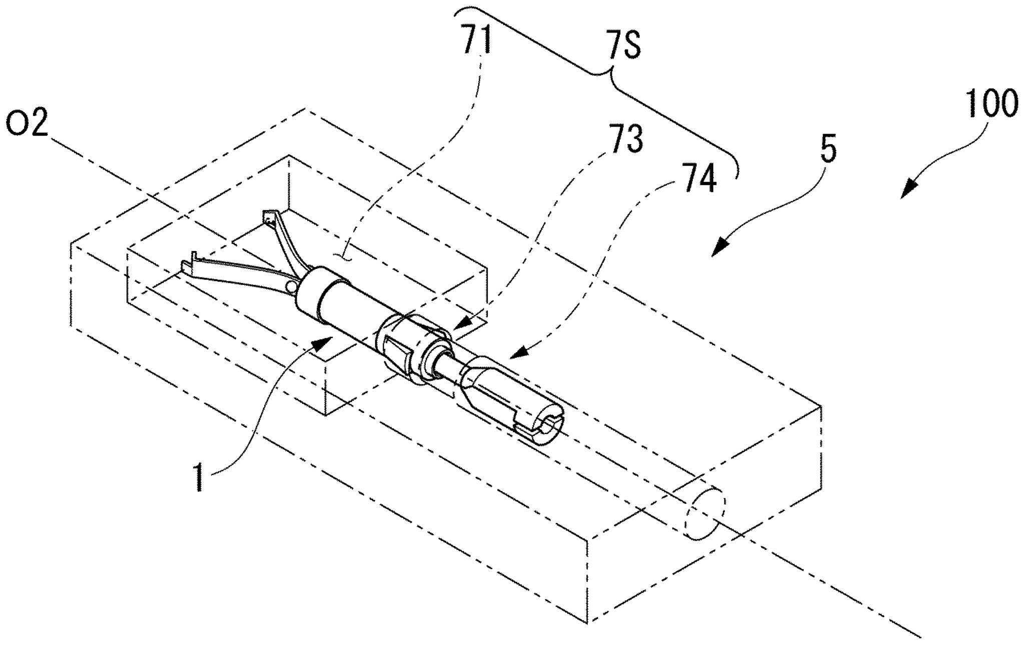
FIG. 13 is a perspective view showing a cartridge in which the clip unit is accommodated.
Figure 13:
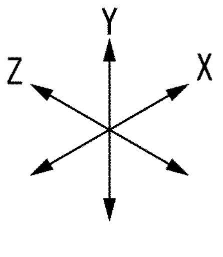

FIG. 13 is a perspective view showing the cartridge 5 in which the clip unit 1 is accommodated.

A system including the clip unit 1 and the cartridge 5 capable of housing the clip unit 1 is referred to as a cartridge system 100. The cartridge system 100 is a support system for easily loading the clip unit 1 into the clip introduction device 200.

The cartridge 5 is a case capable of accommodating the clip unit 1. The cartridge 5 is formed in a size that is easy to hold in the hand such that the width is about 10 to 20 mm, the length is about 50 mm, and the thickness is about 5 mm.

The cartridge 5 is manufactured by injection molding using a transparent resin material having a suitable hardness, such as ABS, PC, PP, PS, acrylic, or cycloolefin polymer. The cartridge 5 is made of a transparent resin material, so that the user can easily determine whether the clip unit 1 is present inside.

As shown in FIG. 13, one of two directions perpendicular to the longitudinal direction Z of the cartridge 5 and perpendicular to each other is referred to as the "left and right direction X" and the other is referred to as the "height direction Y." Further, in the cartridge 5 accommodating the clip unit 1, the side of the pair of arms 21 is referred to as the distal end side Z1 of the cartridge 5, and the side of the connecting member 4 is referred to as the proximal end side Z2 of the cartridge 5.

As shown in FIG. 13, the cartridge 5 has a cartridge body 70 formed in a substantially rectangular box shape and an accommodation region 7S formed inside the cartridge body 70.

The cartridge body 70 is provided with the accommodation region 7S in which the clip unit 1 is accommodated so as to be movable in the longitudinal direction (advance and retreat direction) Z. The accommodation region 7S has a first region 71, a folding region 73, and a sheath insertion region

74. As shown in FIG. 13, the first region 71, the folding region 73, and the sheath insertion region 74 are arranged from the distal end to the proximal end in the longitudinal direction Z of the cartridge 5.

The cartridge body 70 is provided with an insertion opening 67 into which the sheath 220 can be inserted. The opening surface of the insertion opening 67 is formed substantially perpendicular to the longitudinal direction Z. The insertion opening 67 is formed in a side surface of the cartridge body 70 on the proximal end side Z2. The insertion opening 67 communicates with the sheath insertion region 74.

The first region 71 is an internal space in which the clip unit 1 is accommodated to be movable in the longitudinal direction Z. The first region 71 communicates with the folding region 73.

The folding region 73 is a region for maintaining the protruding/retracting wing 31 in a retracted state. The folding region 73 is provided with a reduced diameter portion 73*c* (see FIG. 15). When the clip unit 1 is accommodated in the cartridge 5, the reduced diameter portion 73*c* can hold the connecting arm 44 of the connecting member 4 in a state where the connecting arm 44 is prevented from spreading.

The sheath insertion region 74 is a region into which the distal end portion of the sheath 220 having passed through the insertion opening 67 is inserted. The sheath insertion region 74 is located on the proximal end side Z2 of the folding region 73 and communicates with the folding region 73. At the portion where the sheath insertion region 74 is connected to the region 73, the length of the sheath insertion region 74 in the left and right direction X is longer than the length of the folding region 73 in the left and right direction X.

[Fulcrum Raised Portion 8]

As shown in FIG. 1, the arm 21 is provided with a fulcrum raised portion (bump, convex portion) 8. The fulcrum raised portion 8 is provided at the proximal end portion 29 of the arm 21. In an insertion form Pi, the arm 21 is pivotable about the fulcrum raised portion 8 relative to the pressing member 3. Furthermore, the arm 21 may not be provided with the fulcrum raised portion 8. It is only necessary that the arm 21 has a configuration that allows the arm 21 to pivot about the proximal end portion 29 of the arm 21 relative to the pressing member 3 in the insertion form Pi.

Figure 29:
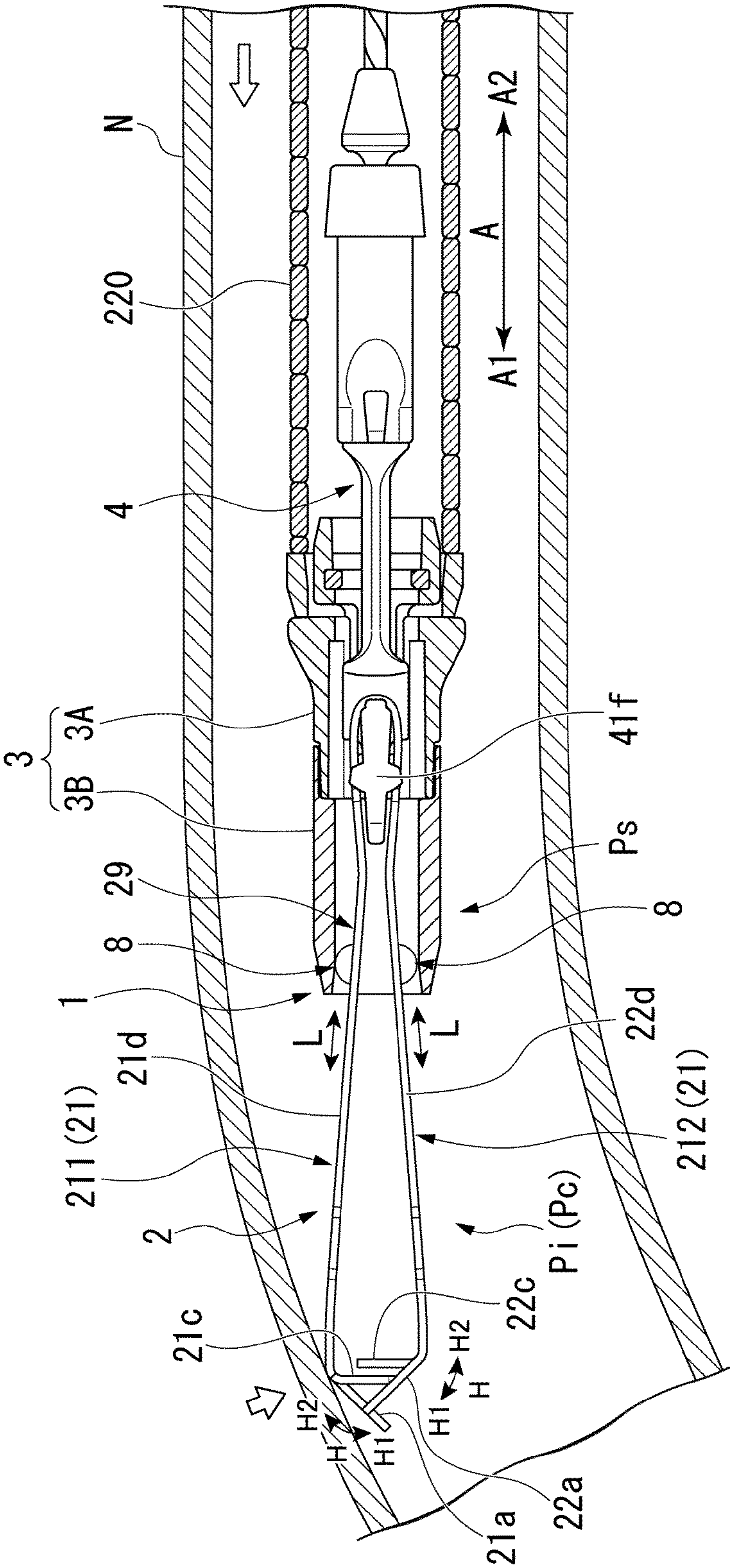
FIG. 29 is a perspective view showing the clip device and showing a state where the first arm comes into contact with a treatment tool insertion channel of an endoscope.
Figure 30:
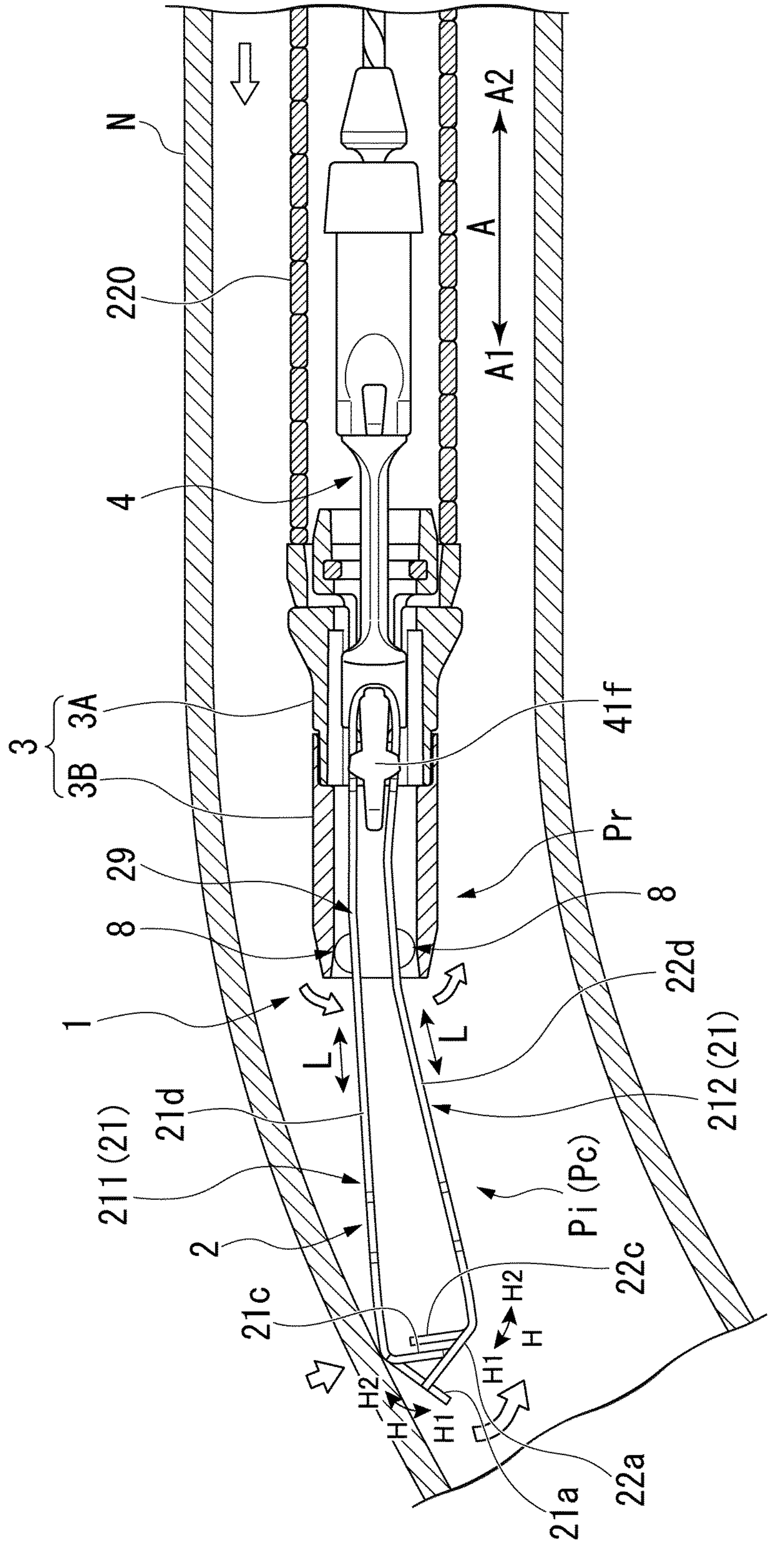
FIG. 30 is a perspective view showing the clip device and showing an arm pivoting about a fulcrum raised portion relative to the pressing member.

The insertion form Pi is a form in which the first arm 211 and the second arm 212 can be inserted through the treatment tool insertion channel (channel) N of the endoscope in a closed state as shown in FIG. 1 (see FIGS. 29 and 30). The insertion form Pi is included in the closed form Pc. The closed form Pc includes a form in which the clip 2 is locked (see FIG. 27), while the insertion form Pi is a state where the clip 2 is not locked.

The first arm 211 and the second arm 212 can transition between a straight state Ps and a bent state Pr in the insertion form Pi. The straight state Ps is a state where the longitudinal direction L and the longitudinal direction A of the first arm 211 and the second arm 212 substantially coincide with each other in the insertion form Pi. The bent state Pr is a state where the longitudinal direction L and the longitudinal direction A of the first arm 211 and the second arm 212 intersect with each other in the insertion form Pi. When the first arm 211 and the second arm 212 pivot relative to the pressing member 3, they transition between the straight state Ps and the bent state Pr.

The fulcrum raised portion 8 is a member that protrudes from the first arm body 21*d* and the second arm body 22*d* toward the opening side H2 in the opening and closing direction H. The two fulcrum raised portions 8 are provided with the proximal end portion 29 interposed therebetween in the opening and closing direction H. The fulcrum raised portion 8 is provided at the proximal end portion 29 of the first arm body 21*d*. Further, the fulcrum raised portion 8 is provided at the proximal end portion 29 of the second arm body 22*d*.

The fulcrum raised portion 8 is curved while protruding toward the opening side H2 in the opening and closing direction H when viewed from the width direction W. The fulcrum raised portion 8 is rounded on the opening side H2 in the opening and closing direction H. The fulcrum raised portion 8 is formed to be rotatable inside the pressing member 3 in the insertion form Pi. The fulcrum raised portion 8 slidably contacts the inner wall of the pressing member 3 in the insertion form Pi. The fulcrum raised portion 8 is formed in a substantially semicircular shape when viewed from the width direction W. Furthermore, the shape of the fulcrum raised portion 8 is not limited.

The fulcrum raised portion 8 may be curved while protruding toward the opening side H2 in the opening and closing direction H when viewed from the longitudinal direction L. The fulcrum raised portion 8 may be formed in a substantially semicircular shape when viewed from the longitudinal direction L. The fulcrum raised portion 8 may be formed so that the first arm 211 and the second arm 212 is pivotable in the width direction W in the insertion form Pi. The fulcrum raised portion 8 may be formed, for example, in a hemispherical shape.

The fulcrum raised portion 8 is a member that protrudes toward the inner wall of the pressing member 3 from the first arm body 21*d* in the insertion form Pi. The fulcrum raised portion 8 is a member that protrudes toward the inner wall of the pressing member 3 from the second arm body 22*d* in the insertion form Pi.

Figure 14:
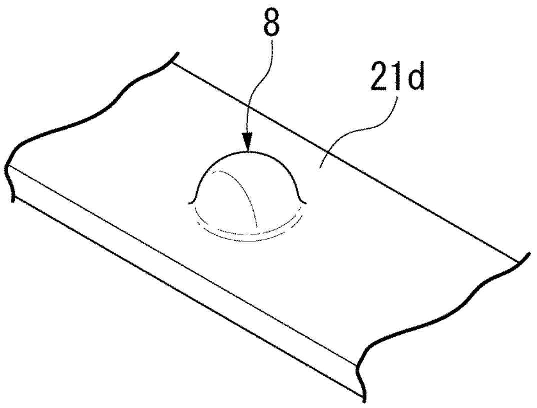
FIG. 14 is a detailed view showing a fulcrum raised portion and showing an example formed by extruding.
Figure 15:
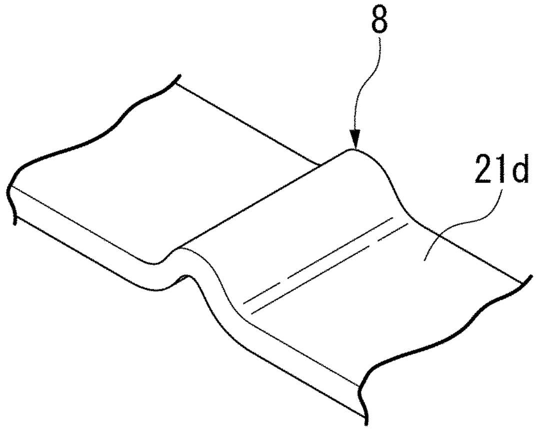
FIG. 15 is a detailed view showing the fulcrum raised portion and showing an example formed by bending.

FIG. 14 is a detailed view showing the fulcrum raised portion 8 and showing an example formed by extruding. FIG. 15 is a detailed view showing the fulcrum raised portion 8 and showing an example formed by bending.

As shown in FIG. 14, the fulcrum raised portion 8 is formed by extruding the first arm body 21*d* and the second arm body 22*d* toward the opening side H2 in the opening and closing direction H. Furthermore, the configuration of the fulcrum raised portion 8 is not limited. For example, the fulcrum raised portion 8 may be formed by bending the first arm body 21*d* and the second arm body 22*d* as shown in FIG. 15.

The fulcrum raised portion 8 is disposed inside the pressing member 3 in the insertion form Pi. The fulcrum raised portion 8 comes into contact with the inside of the pressing member 3 in the insertion form Pi. Since the fulcrum raised portion 8 receives a force directed from the pressing member 3 toward the closing side H1 in the opening and closing direction H when the fulcrum raised portion 8 is pulled from the outside to the inside of the pressing member 3, the first arm body 21*d* and the second arm body 22*d* transition to the insertion form Pi.

When the first arm 211 and the second arm 212 transition from the straight state Ps to the bent state Pr, the fulcrum raised portion 8 moves toward the distal end side A1 in the longitudinal direction A relative to the pressing member 3. That is, in the bent state Pr, the fulcrum raised portion 8 is located on the distal end side A1 in relation to the position for the pressing member 3 in the straight state Ps.

Furthermore, when the first arm 211 and the second arm 212 transition from the straight state Ps to the bent state Pr, the position to which the fulcrum raised portion 8 moves relative to the pressing member 3 is not limited. For example, in the bent state Pr, the fulcrum raised portion 8 may be located closer to the proximal end side A2 than the position of the fulcrum raised portion 8 relative to the pressing member 3 in the straight state Ps. Furthermore, in the bent state Pr, one of the pair of fulcrum raised portions 8 may be located on the distal end side A1 in relation to the position relative to the pressing member 3 in the straight state Ps, and the other may be located on the proximal end side A2 in relation to the position relative to the pressing member 3 in the straight state Ps.

[Method of Loading Clip Unit 1]

Next, the action of the cartridge system 100 will be described with reference to FIGS. 16 to 22.

Figure 16:
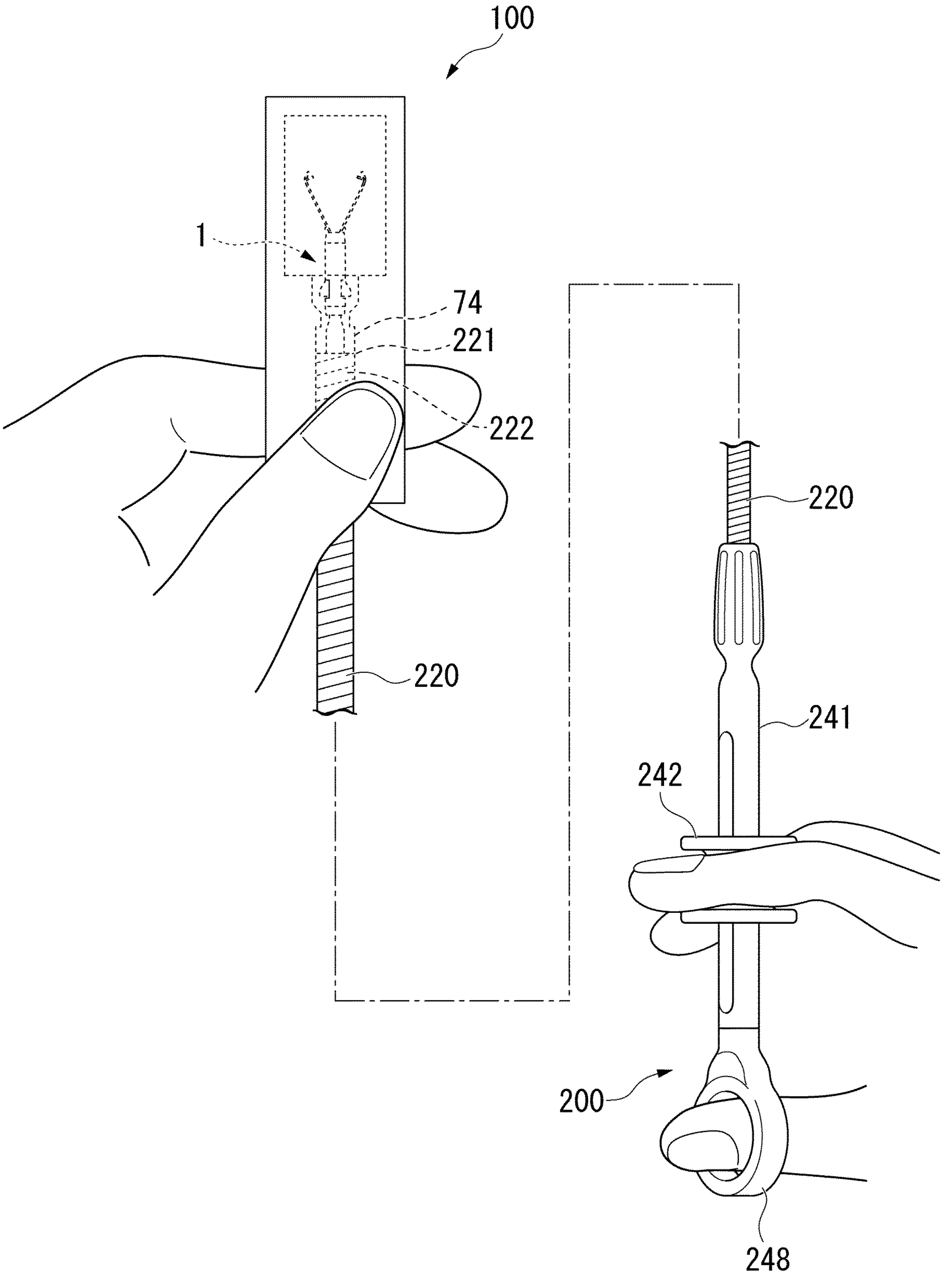
FIG. 16 is a diagram showing an operation of loading the clip unit.

FIG. 16 is a diagram showing an operation of loading the clip unit 1. FIGS. 17 to 22 are views illustrating a method of loading the clip unit 1 into the clip introducing device 200 using the cartridge 5.

The user inserts the sheath 220 from the insertion opening 67 into the sheath insertion region 74.

Figure 17:
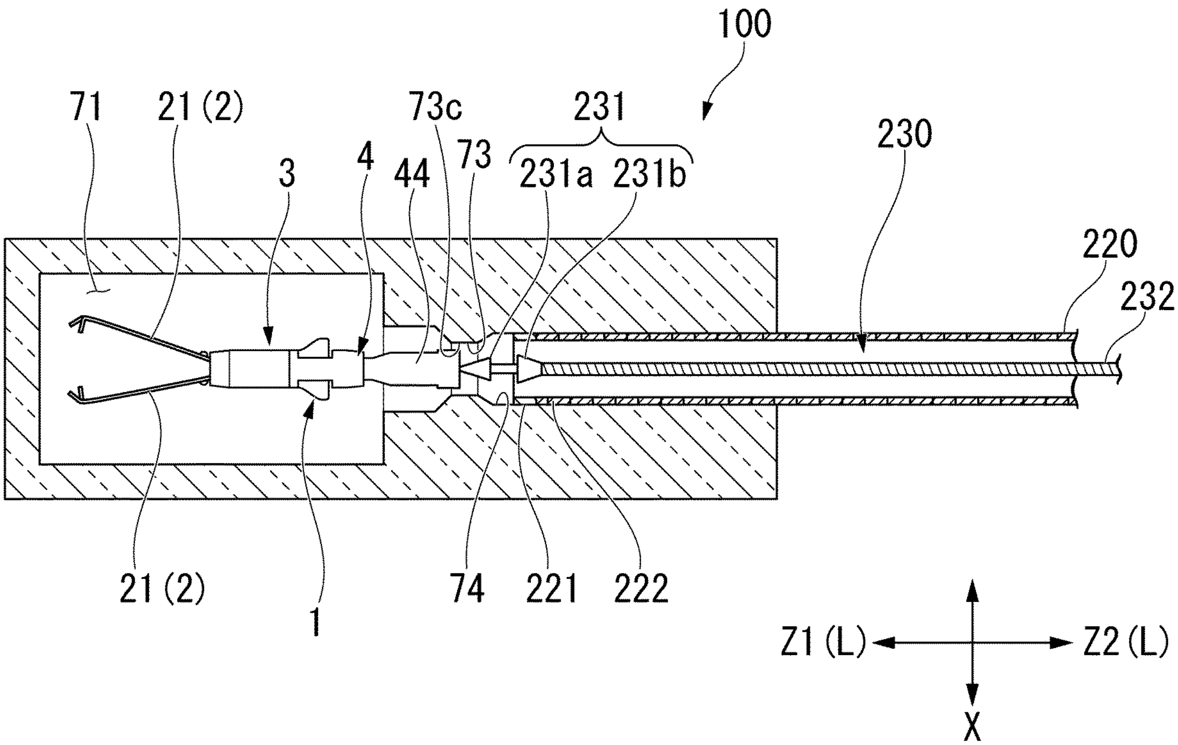
FIG. 17 is a diagram illustrating a method of loading the clip unit into the clip introducing device using the cartridge.

FIG. 17 is a diagram showing the clip unit 1 connected to the clip introducing device 200.

The user advances the clip unit 1 until the clip unit 1 contacts the cartridge 5 by pressing the connecting member 4 with the arrowhead hook 231 in such a manner that the slider 242 is advanced relative to the operation unit body 241 of the operation unit 240 to advance the operating wire 230 relative to the sheath 220.

Figure 18:
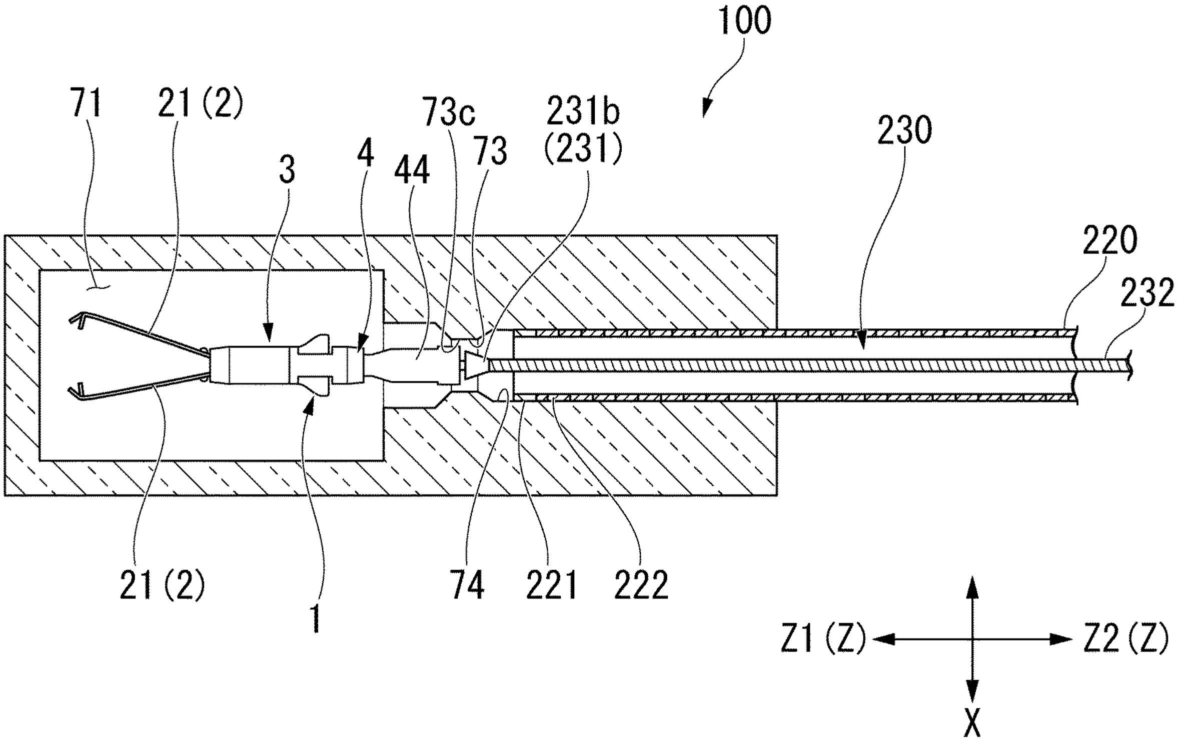
FIG. 18 is a diagram illustrating a method of loading the clip unit into the clip introducing device using the cartridge.

FIG. 18 is a diagram showing the clip unit 1 connected to the clip introducing device 200.

The user further advances the arrowhead hook 231 to connect the engagement portion 231*a* of the arrowhead hook 231 to the connecting arm 44 of the connecting member 4.

Figure 19:
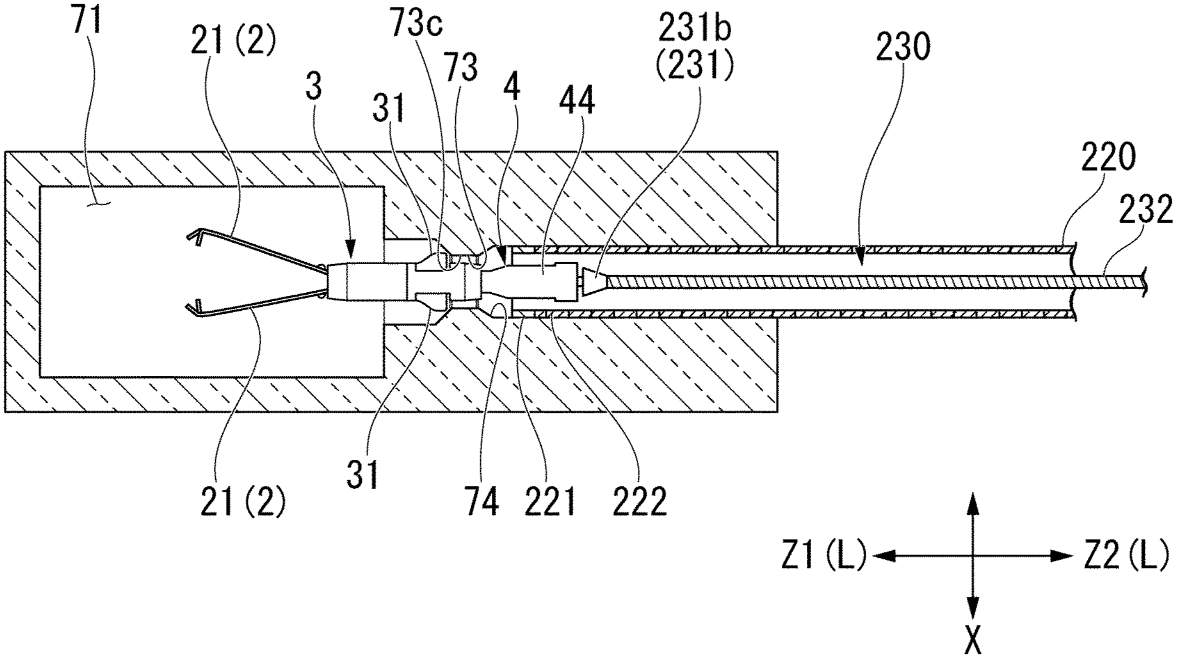
FIG. 19 is a diagram illustrating a method of loading the clip unit into the clip introducing device using the cartridge.

As shown in FIG. 19, the user pulls the operating wire 230. The clip 2 of the clip unit 1 is pulled toward the proximal end side Z2 by the connecting member 4 connected to the arrowhead hook 231.

Figure 20:
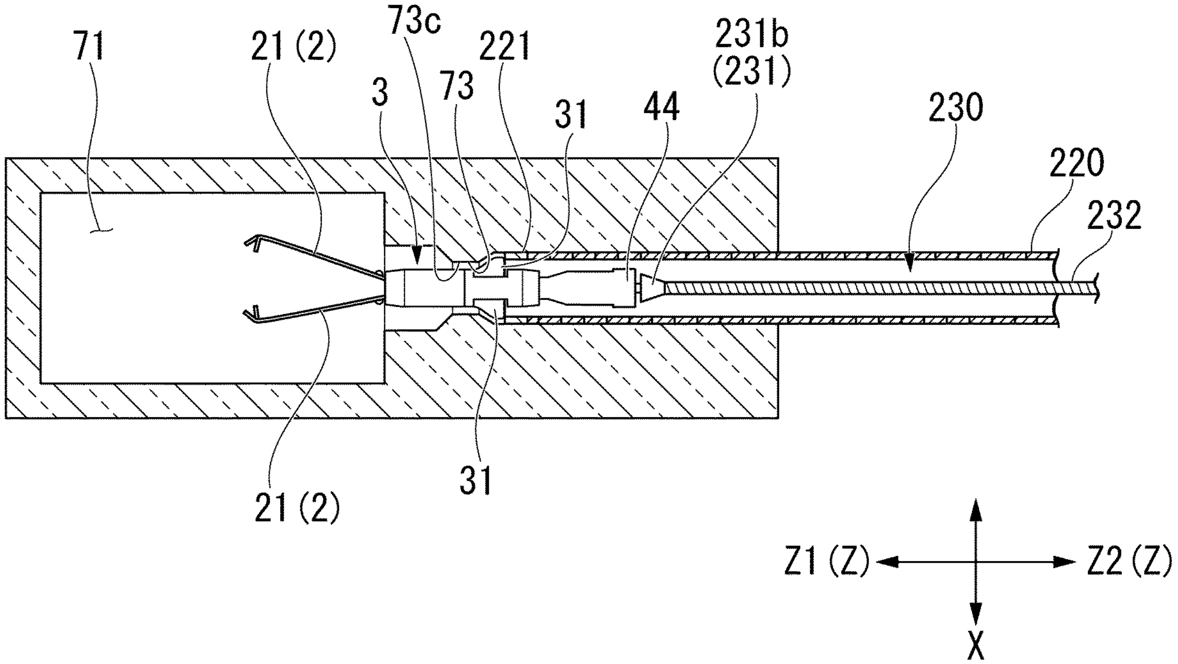
FIG. 20 is a diagram illustrating a method of loading the clip unit into the clip introducing device using the cartridge.

The user further pulls the clip unit 1 toward the proximal end side Z2. As shown in FIG. 20, the proximal end of the protruding/retracting wing 31 comes into contact with the distal end of the sheath 220.

Figure 21:
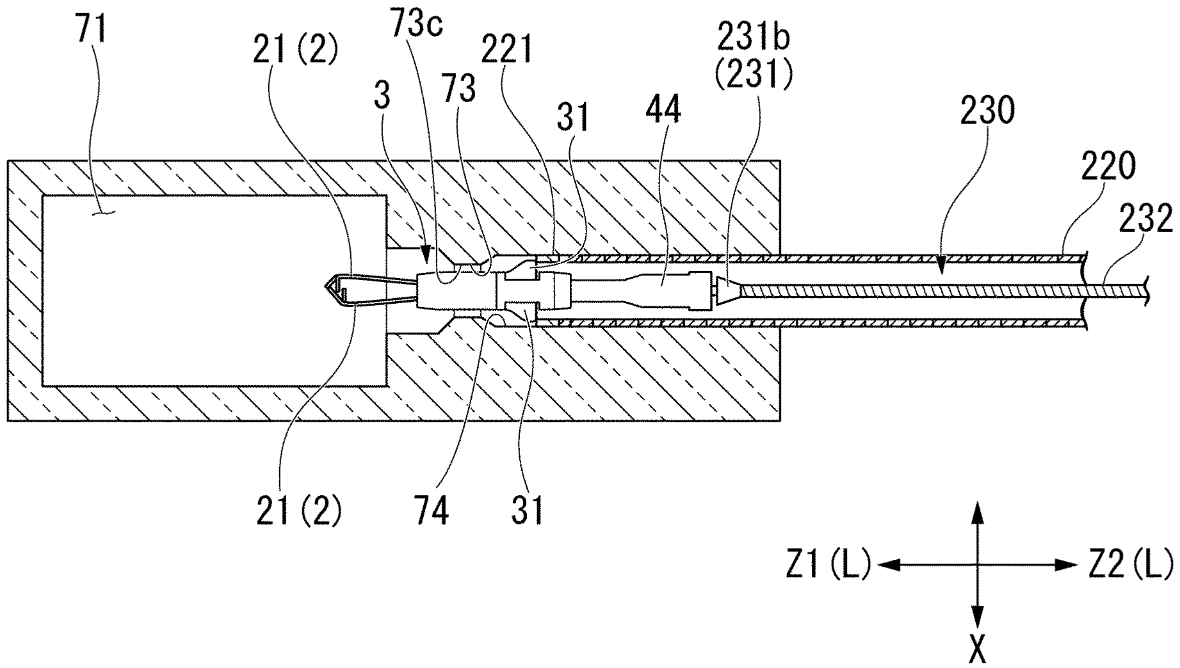
FIG. 21 is a diagram illustrating a method of loading the clip unit into the clip introducing device using the cartridge.

As shown in FIG. 21, the user further pulls the operating wire 230. The clip 2 pulled toward the proximal end side Z2 is pulled into the internal space of the pressing tube 3A and into the sheath 220. Accordingly, the loading of the clip unit 1 into the clip introducing device 200 is completed. At this time, the clip 2 is not completely pulled into the sheath 220. As shown in FIG. 21, the clip 2 is loaded in a state where the clip 2 protrudes from the distal end of the sheath 220.

Figure 22:
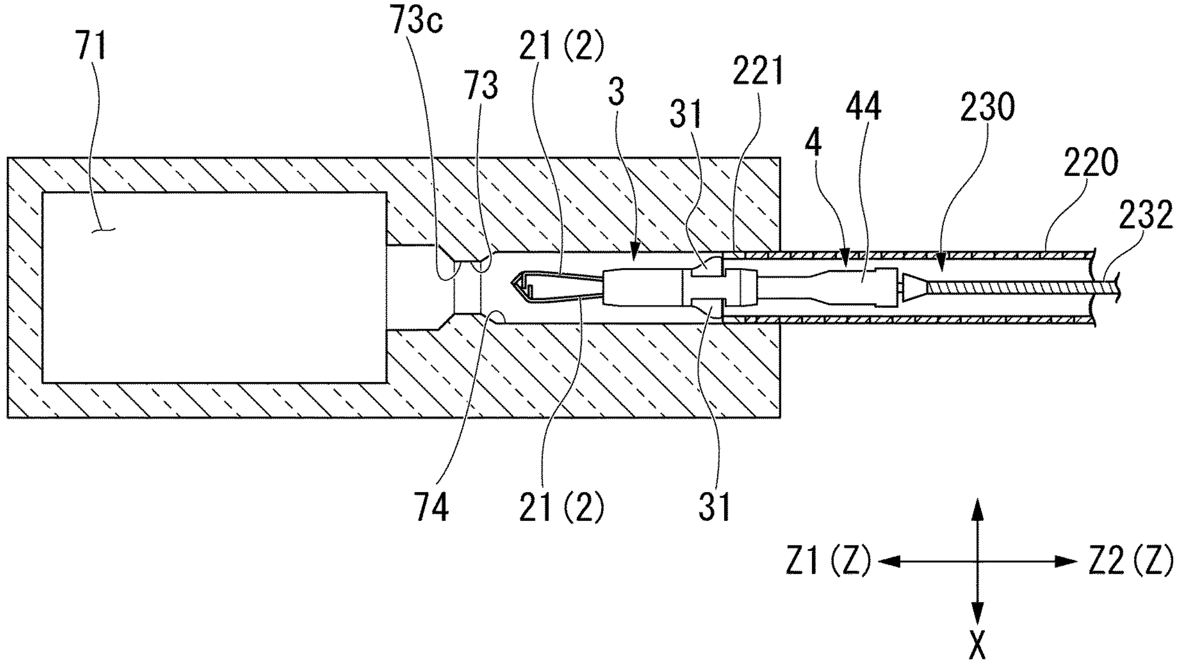
FIG. 22 is a diagram illustrating a method of loading the clip unit into the clip introducing device using the cartridge.

As shown in FIG. 22, the user further pulls the operating wire 230. The clip 2 is pulled out from the cartridge 5 in a state where the clip 2 protrudes from the distal end of the sheath 220.

[Operation and Action of Clip Unit 1]

Next, the operation and action of the clip unit 1 will be described with reference to FIGS. 23 to 28.

Figure 23:
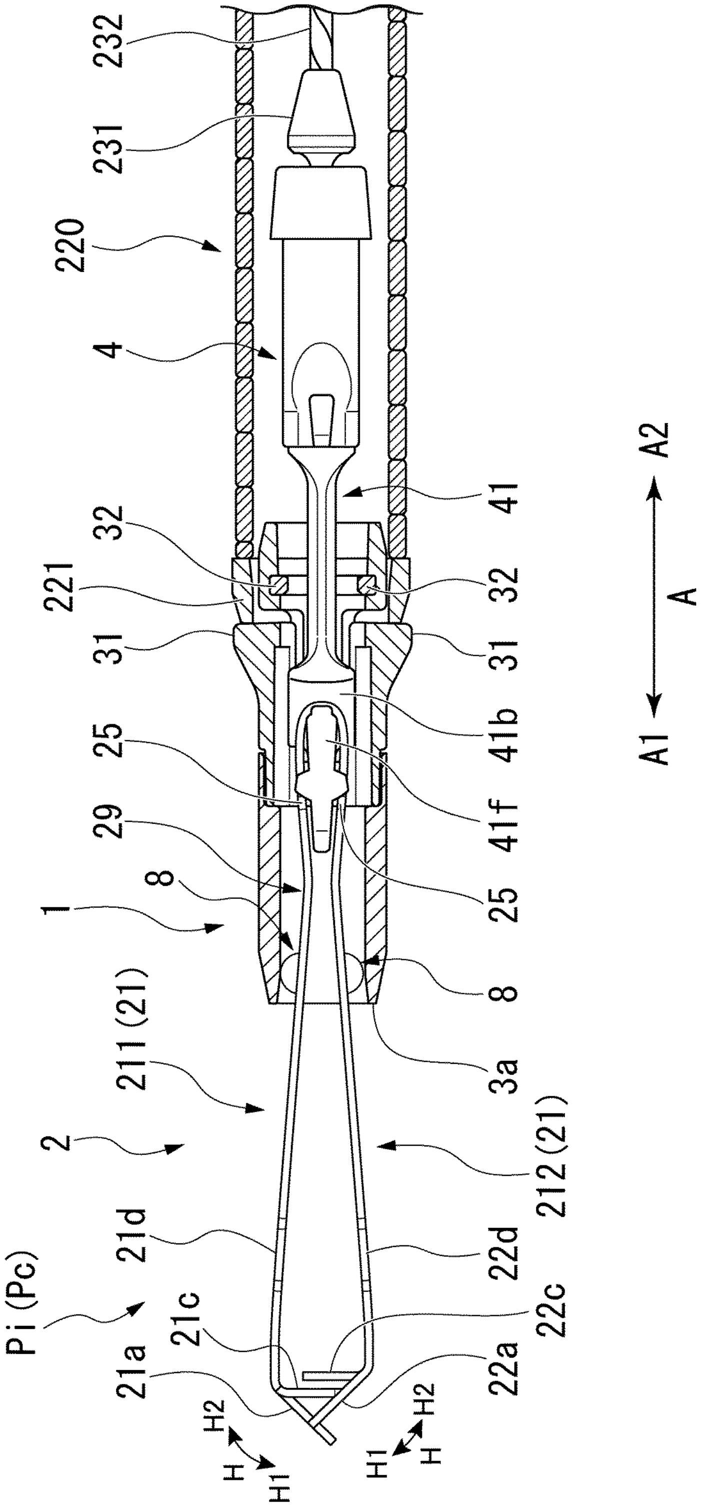
FIG. 23 is a diagram showing the clip unit loaded into the clip introducing device.

FIG. 23 is a diagram showing the clip unit 1 loaded into the clip introducing device 200.

The clip unit 1 is loaded into the clip introducing device 200 using the cartridge 5. The connecting member 4 of the clip unit 1 loaded into the clip introducing device 200 is connected to the arrowhead hook 231 inserted through the sheath 220. The protruding/retracting wing 31 is disposed at the distal end of the sheath 220. The clip 2 protrudes from the distal end of the sheath 220.

The pair of arms 21 of the loaded clip unit 1 are pressed against the inner peripheral surface of the sheath 220 via the fulcrum raised portion 8 to be closed. The engagement portion 25 is located on the distal end side A1 in relation to the fastening member 32, and the pair of arms 21 are not locked in the closed form Pc. At this time, the pair of arms 21 are in the insertion form Pi.

Figure 24:
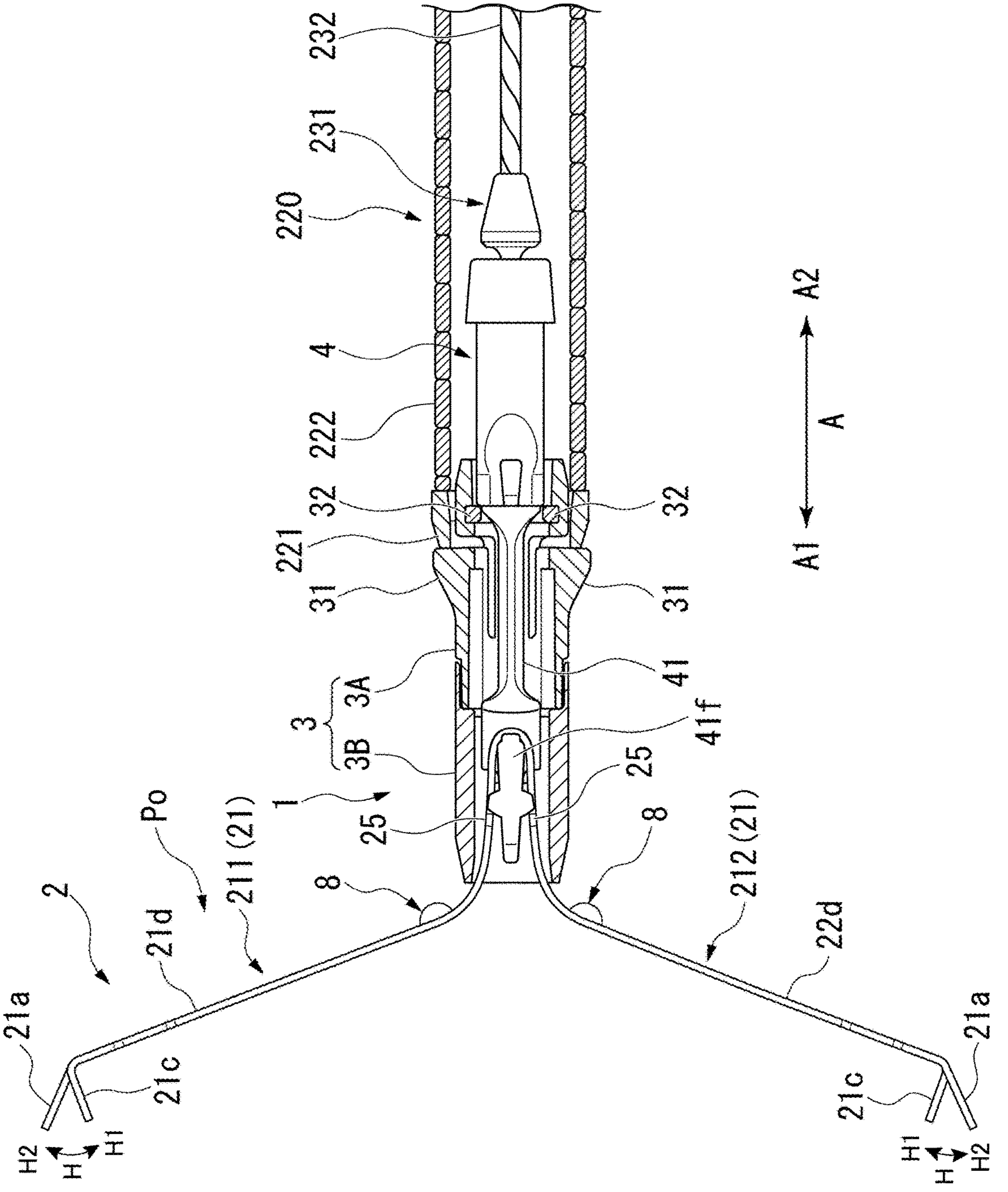
FIG. 24 is a diagram showing the clip unit in an open form.

FIG. 24 is a diagram showing the clip unit 1 in the open form Po.

The user introduces the clip unit 1 loaded into the sheath 220 into the body via the treatment tool insertion channel N of the endoscope. Next, the user advances the slider 242 along the operation unit body 241 to advance the arrowhead hook 231.

When the distal end side A1 of the pair of arms 21 comes out of the sheath 220, the self-expanding force of the pair of arms 21 serves as a restoring force, and the clip 2 returns to the open form Po while moving toward the distal end side A1 relative to the pressing member 3. Even when the pair of arms 21 return to the open form Po and protrude to the maximum from the pressing member 3, the engagement portion 25 is disposed in the internal space 38 of the pressing member 3.

The user retracts the slider 242 along the operation unit body 241 to retract the arrowhead hook 231. The connecting member 4 connected to the arrowhead hook 231 pulls the clip 2. The pair of arms 21 having a self-expanding force are pulled toward the proximal end side A2 to press the distal end opening 3*a* of the pressing member 3 toward the proximal end side A2 via the fulcrum raised portion 8. Since the protruding/retracting wing 31 engages with the sheath 220, the protruding/retracting wing is not pulled into the sheath 220. Therefore, the clip 2 pulled by the connecting member 4 is pulled into the pressing member 3.

When the connecting portion 28 of the clip 2 is pulled toward the proximal end side A2 of the pressing member 3 by the connecting member 4, the pair of arms 21 are pulled into the pressing member 3 and the pair of arms 21 are gradually closed. When the pulling force of the connecting portion 28 is released in this state, the clip 2 returns to the open form Po while moving toward the distal end side A1 using the self-expanding force of the pair of arms 21 as a restoring force. The user can return the pair of arms 21 to the open form Po to grasp the tissue again.

The user moves the endoscope and the sheath 220 to bring the clip 2 of the clip unit 1 closer to a defect D, which is a treatment region. In the following description, the mucosa surrounding the defect D and arranged opposite each other across the defect D are referred to as the "first mucosa M1" and the "second mucosa M2."

Figure 25:
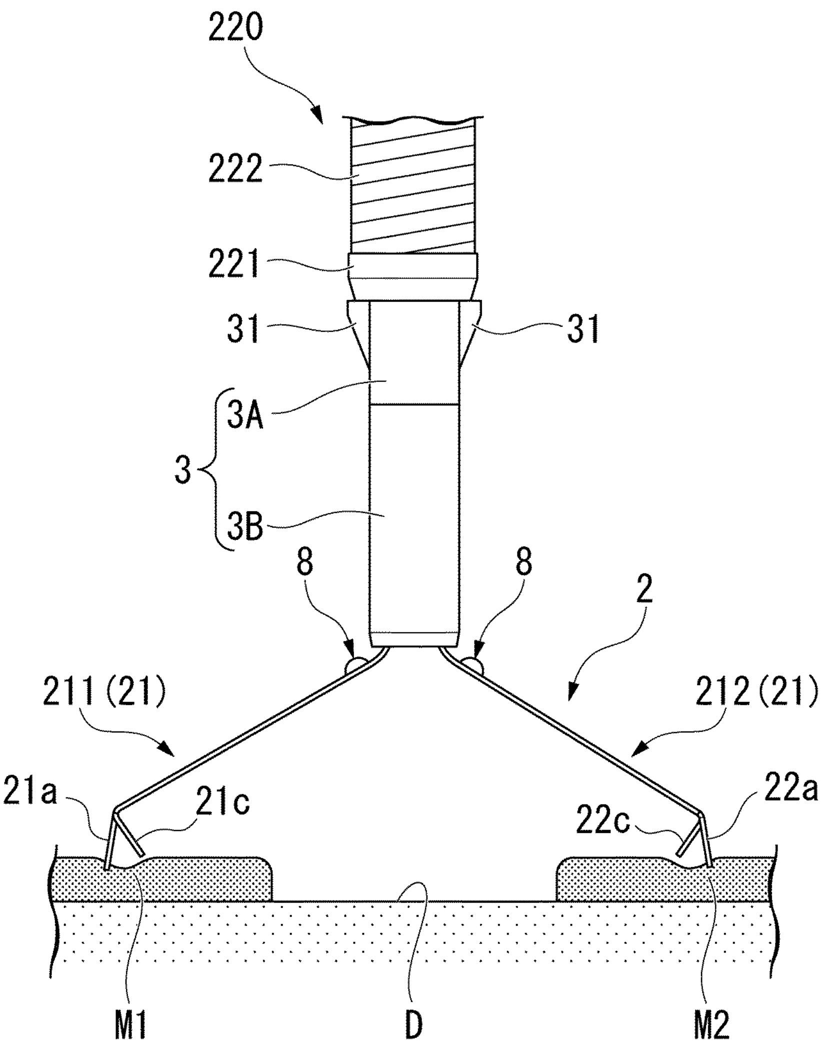
FIG. 25 is a diagram showing a first anchor and a second anchor that have punctured the mucosa.

FIG. 25 is a diagram showing the first anchor 21*a* and the second anchor 22*a* that have punctured the mucosa. The user punctures the first mucosa M1 with the first anchor 21*a* and punctures the second mucosa M2 with the second anchor 22*a*. The first anchor 21*a* and the second anchor 22*a* extend toward the closing side H1 in the opening and closing direction H, but are arranged on the opening side H2 in the opening and closing direction H in relation to the first claw 21*c* and the second claw 22*c*. Therefore, when the clip 2 in the open form Po is disposed in front of the mucosa, the first anchor 21*a* and the second anchor 22*a* are arranged so as to easily puncture the mucosa.

Figure 26:
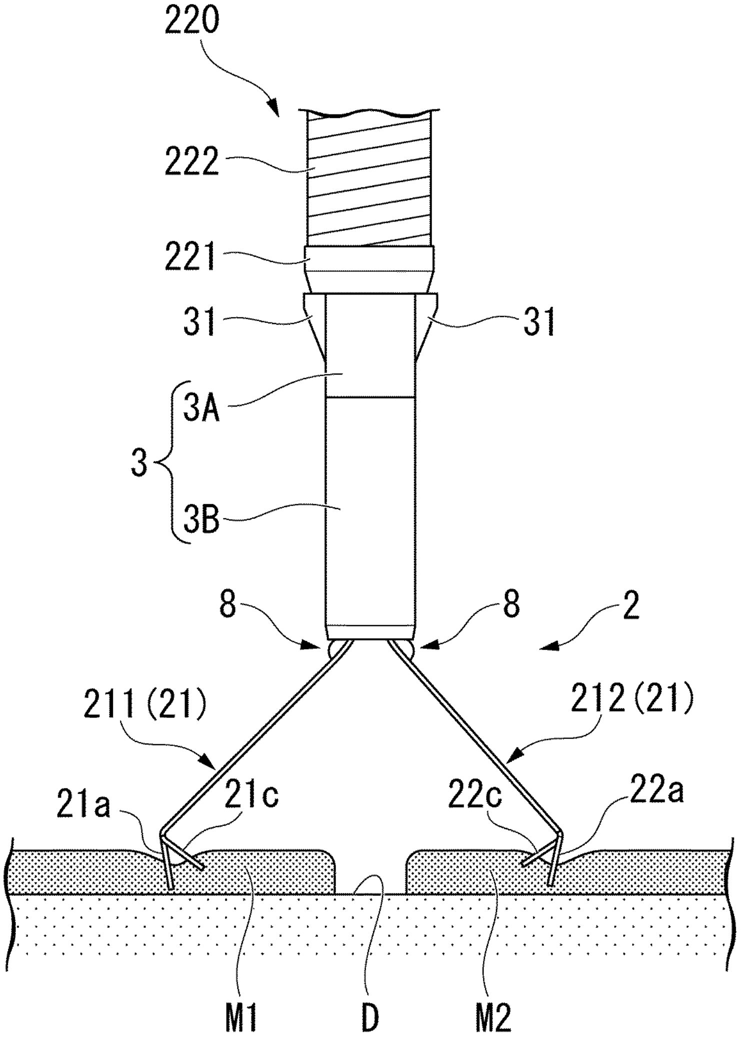
FIG. 26 is a diagram showing a first mucosa and a second mucosa brought together.

FIG. 26 is a diagram showing the first mucosa M1 and the second mucosa M2 that are pulled together.

The user can pull together the first mucosa M1 and the second mucosa M2 by pulling together the first arm 211 having the first anchor 21*a* punctured the first mucosa M1 and the second arm 212 having the second anchor 22*a* punctured the second mucosa M2.

Figure 27:
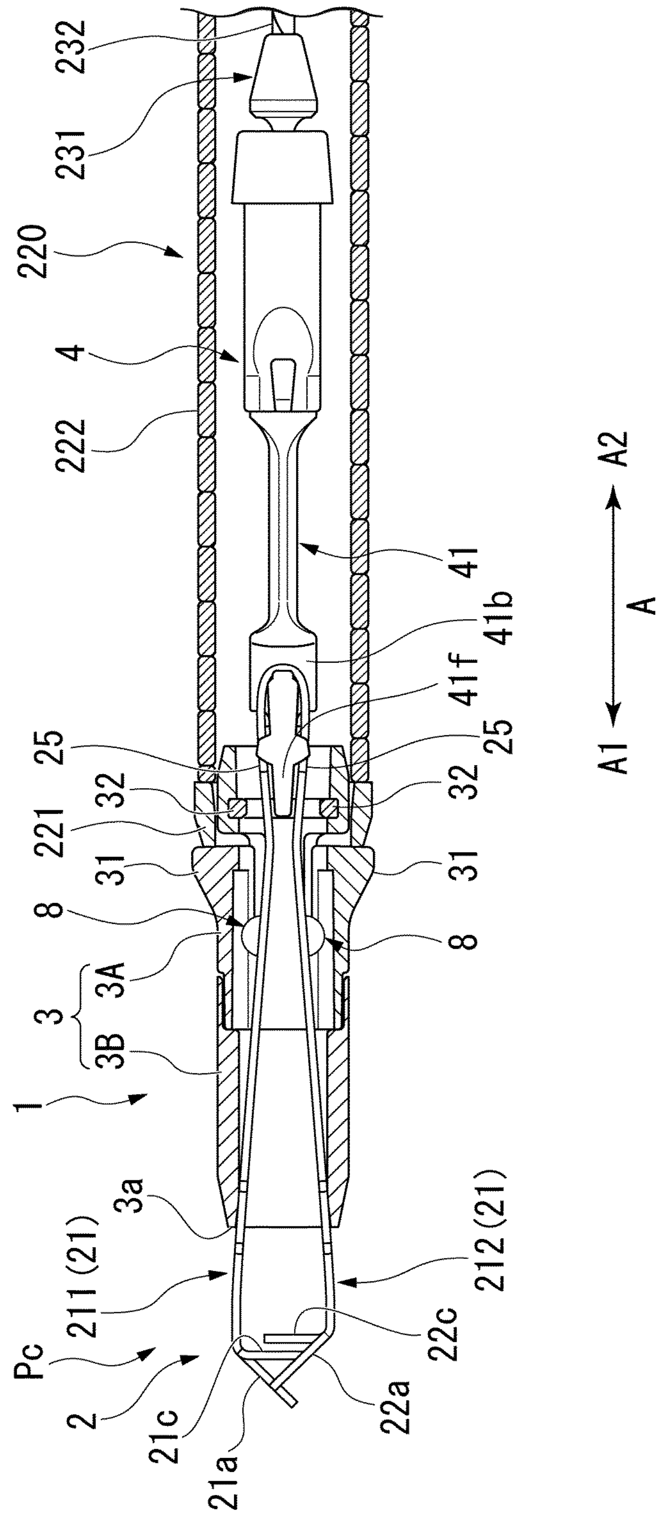
FIG. 27 is a diagram showing the clip unit in which the clip is locked.

FIG. 27 is a diagram showing the clip unit 1 with the clip 2 locked.

When the connecting portion 28 is further pulled toward the proximal end side A2 of the pressing member 3, the engagement portion 25 is pulled toward the proximal end side A2 in relation to the fastening member 32. Since the proximal end side A2 of the engagement portion 25 is formed as an obtuse inclined surface, the engagement portion 25 is more easily pulled toward the base end side A2 in relation to the fastening member 32. On the other hand, since the distal end side A1 of the engagement portion 25 is formed into an acute inclined surface, the engagement portion 25 engages with the fastening member 32 when the engagement portion 25 is pulled to the proximal end side A2 in relation to the fastening member 32. As a result, the movement of the clip 2 toward the distal end side A1 relative to the pressing member 3 is restricted, and the pair of arms 21 are locked in the closed form Pc. When the pair of arms 21 are locked in the closed form Pc, the pair of arms 21 cannot return to the open form Po.

Figure 28:
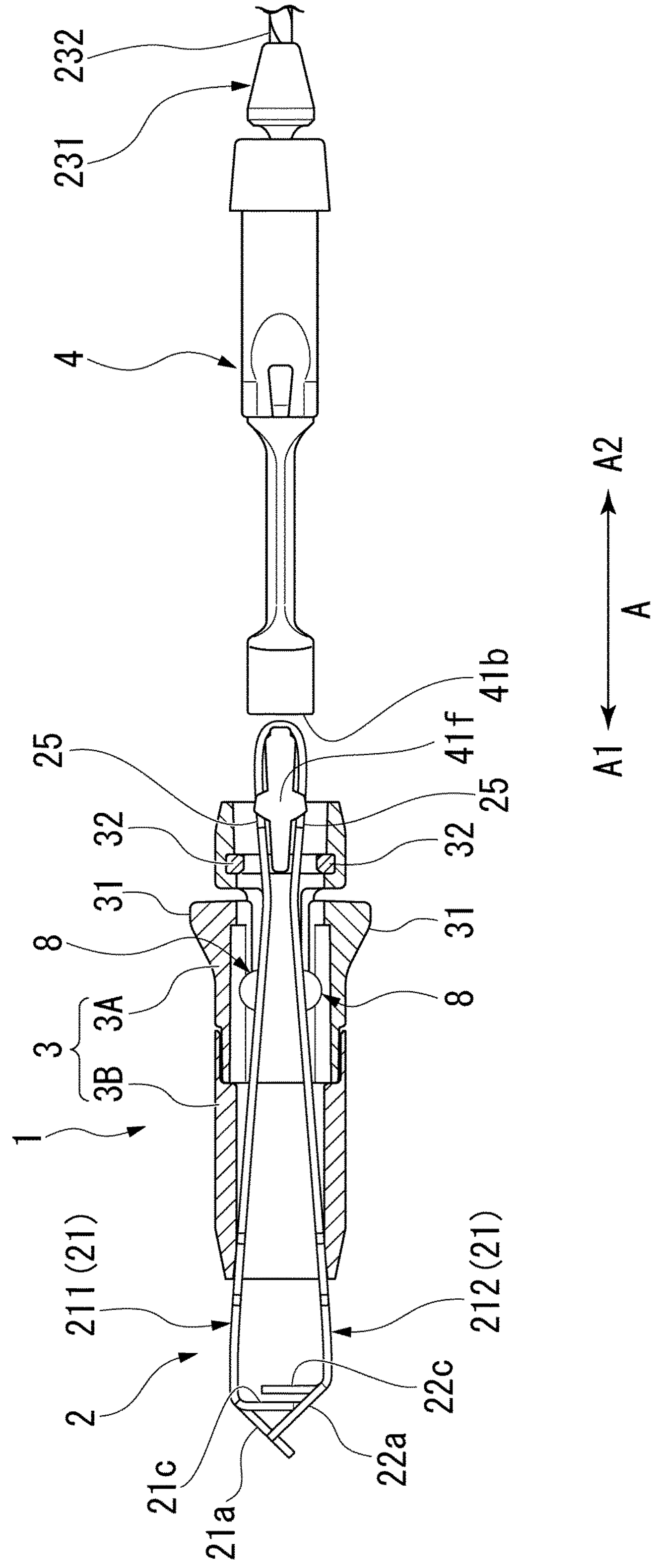
FIG. 28 is a diagram showing the clip unit from which the clip is separated.

FIG. 28 is a diagram showing the clip unit 1 from which the clip 2 is separated.

The user further pulls the clip 2. A breaking force is applied to the hook 41*f* by pulling, and the breakable portion 41*b* breaks. The breaking strength of the breakable portion 41*b* is lower than the breaking strength of the connecting portion body 43. Therefore, the breakable portion 41*b* breaks instead of the connecting portion body 43.

The user reloads a new clip unit 1 into the clip introducing device 200 using the cartridge 5.

[Action of Fulcrum Raised Portion 8]

Next, the action of the fulcrum raised portion 8 will be described with reference to FIGS. 29 and 30.

FIG. 29 is a perspective view showing the clip device 300 and showing a state where the first arm 211 comes into contact with the treatment tool insertion channel N of the endoscope.

The clip device 300 can be inserted through the treatment tool insertion channel N of the endoscope in the insertion form Pi. At this time, the clip device 300 advances in the longitudinal direction A from the proximal end side A2 toward the distal end side A1.

Since the treatment tool insertion channel N of the endoscope is curved, the clip device 300 may come into contact with the treatment tool insertion channel N of the endoscope. For example, as shown in FIG. 29, the first arm 211 contacts the treatment tool insertion channel N of the endoscope. At this time, the first arm 211 receives a force directed from the treatment tool insertion channel N of the endoscope toward the closing side H1 in the opening and closing direction H.

FIG. 30 is a perspective view showing the clip device 300 and showing a state where the arm 21 pivots about the fulcrum raised portion 8 relative to the pressing member 3.

When the first arm 211 receives a force directed from the treatment tool insertion channel N of the endoscope toward the closing side H1 in the opening and closing direction H, as shown in FIG. 30, the first arm 211 pivots about the fulcrum raised portion 8 relative to the pressing member 3. The second arm 212 is linked with the first arm 211 and pivots about the fulcrum raised portion 8 relative to the pressing member 3. Since a clearance is formed between the first and second arms 211 and 212 and the pressing member 3 by forming the fulcrum raised portion 8, the first arm 211 and the second arm 212 are pivotable about the fulcrum raised portion 8 relative to the pressing member 3.

Since the first arm 211 and the second arm 212 pivot about the fulcrum raised portion 8 relative to the pressing member 3 when the first arm 211 and the second arm 212 contact the treatment tool insertion channel N of the endoscope, the distal ends of the first anchor 21*a* and the second anchor 22*a* can be prevented from coming into contact with the treatment tool insertion channel N of the endoscope. Therefore, the clip device 300 has good insertability.

Since the fulcrum raised portion 8 is provided, it is possible to prevent the user from unintentionally locking or releasing the clip 2.

In the process of loading the clip 2 or performing a treatment using the clip 2, the user transitions the clip 2 from the open form Po to the insertion form Pi. At this time, the fulcrum raised portion 8 is housed in the pressing member 3. When the fulcrum raised portion 8 is housed in the pressing member 3, the clip 2 receives a force from the pressing member 3 via the fulcrum raised portion 8, so that the user feels an increased sense of force. That is, when the fulcrum raised portion 8 is housed in the distal end of the pressing member 3 and the clip 2 transitions from the open form Po to the insertion form Pi, the user feels a change in the amount of force. This change in the amount of force contributes to providing feedback to the user that the clip 2 has transitioned from the open form Po to the insertion form Pi. Therefore, since the fulcrum raised portion 8 is provided, it is easy for the user to notice the transition of the clip 2 from the open form Po to the insertion form Pi and it is possible to prevent the user from unintentionally locking or releasing the clip 2.

According to the clip device 300 of this embodiment, since the fulcrum raised portion 8 is provided, the arm 21 is pivotable about the fulcrum raised portion 8 relative to the pressing member 3, and the distal end of the arm 21 can be prevented from contacting the inner wall of the treatment tool insertion channel N of the endoscope. Therefore, the clip device 300 has good insertability. Since the insertability of the clip device 300 is good, the user can begin treatment of biological tissue as soon as possible.

Although the first embodiment of the present invention has been described in detail above with reference to the drawings, the specific configuration is not limited to this embodiment, and design changes and the like within the scope of the gist of the present invention are also included. Further, the components shown in the above-described embodiment and the modified examples shown below can be appropriately combined to form a configuration.

Second Embodiment

[Clip Device 300*b*]

A clip device 300B according to a second embodiment of the present invention will be described with reference to FIGS. 31 to 38. The clip device 300B according to the second embodiment is different from the clip device 300 according to the first embodiment in the configurations of the clip and the like. In the following description, components common to those already described will be indicated by the same reference numerals and duplicated description will be omitted.

Figure 31:
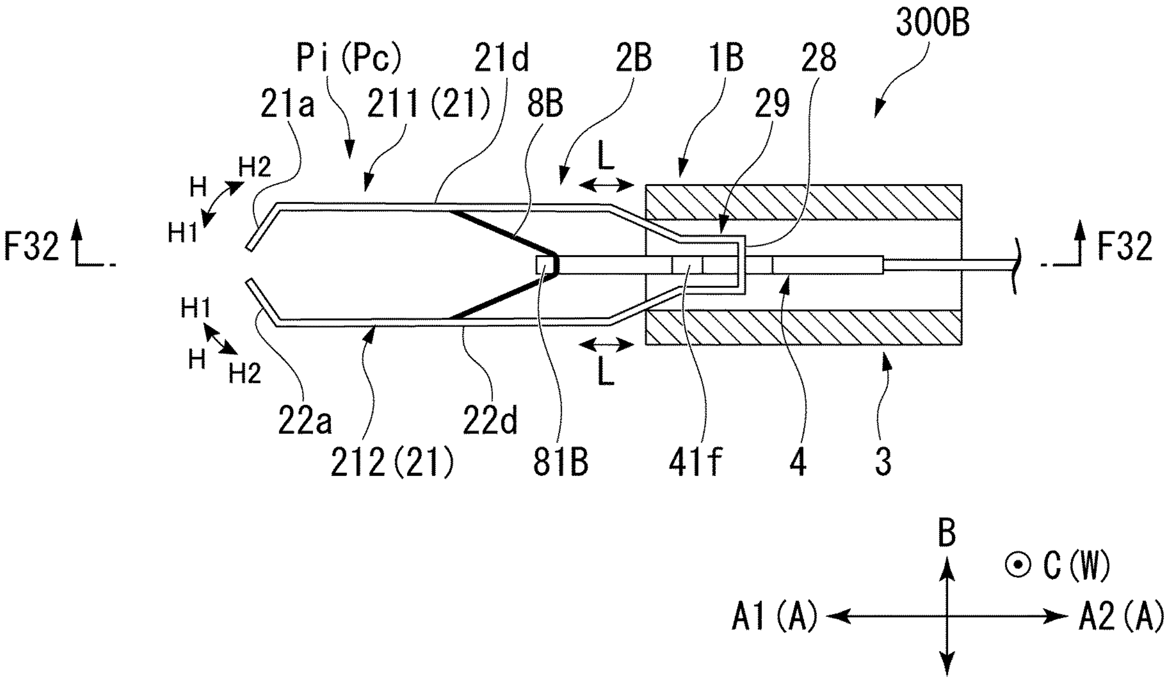
FIG. 31 is a side view showing a clip device according to a second embodiment in a closed form.
Figure 32:
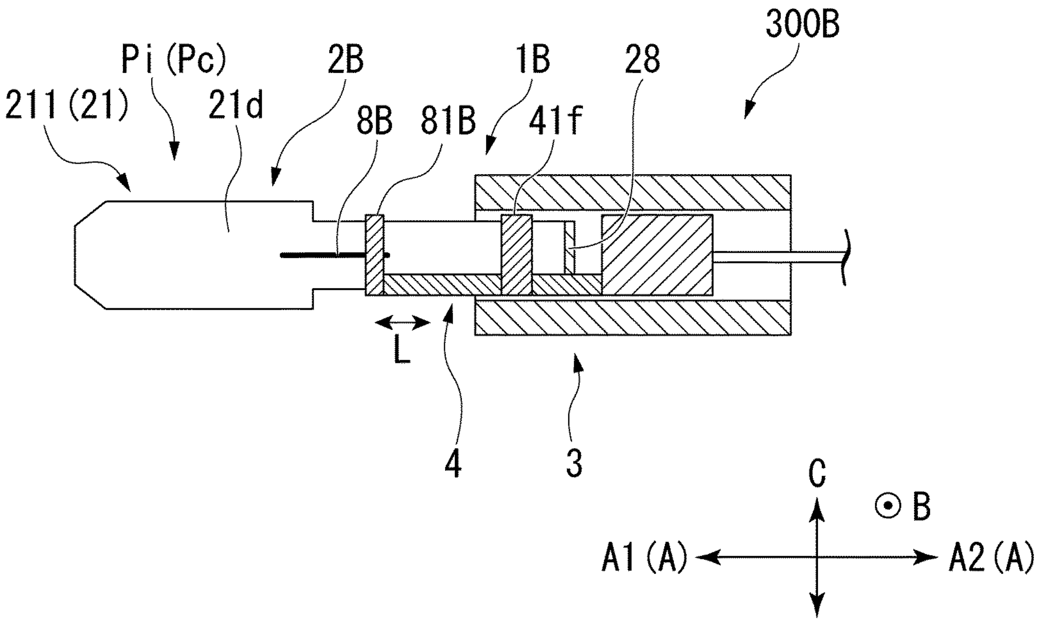
FIG. 32 is a cross-sectional view of the clip device shown in FIG. 31 taken along line F32-F32.

FIG. 31 is a side view showing the clip device 300B in the closed form Pc. FIG. 32 is a cross-sectional view taken along line F32-F32 of the clip device 300B shown in FIG. 31.

The clip device 300B includes the clip introducing device (applicator) 200 and a clip unit 1B. The clip unit 1B is loaded into the clip introducing device 200 as in the clip unit 1. The clip unit 1B is housed in the cartridge 5 as in the clip unit 1.

The clip unit 1B has a clip 2B, the pressing member 3, and the connecting member 4. The clip 2B is supported by the pressing member 3. The clip 2B is connected to the clip introducing device 200 via the connecting member 4.

[Clip 2*b*]

The clip 2B is formed by bending a metal plate material at the center as in the clip 2, and has the first arm 211 and the second arm 212 that are openable and closable. In the insertion form Pi, the clip 2B is provided so as to be pivotable about the proximal end portion 29 of the arm 21 relative to the pressing member 3.

The clip 2B is provided with an opening/closing wire (wire) 8B capable of pulling the first arm 211 and the second arm 212 toward the closing side H1 in the opening and closing direction H. The opening/closing wire 8B is a member capable of closing the first arm 211 and the second arm 212. That is, the opening/closing wire 8B can transition the first arm 211 and the second arm 212 from the open form Po to the closed form Pc. Furthermore, the first arm 211 and the second arm 212 can also transition from the closed form Pc to the insertion form Pi. The first arm 211 and the second arm 212 are pulled toward the closing side H1 in the opening and closing direction H by the opening/closing wire 8B to transition from the open form Po to the closed form Pc.

In this embodiment, the opening/closing wire 8B is connected to the first arm body 21*d* and the second arm body 22*d*. The opening/closing wire 8B connects the first arm body 21*d* to the second arm body 22*d*. Furthermore, the installation position of the opening/closing wire 8B is not limited.

The opening/closing wire 8B is pulled toward the proximal end side A2 in the longitudinal direction A to pull the first arm 211 and the second arm 212 toward the closing side H1 in the opening and closing direction H. In this embodiment, the connecting member 4 is provided with a hook 81B capable of pulling the opening/closing wire 8B toward the proximal end side A2 in the longitudinal direction A.

The hook 81B is a member capable of hooking the opening/closing wire 8B. The hook 81B is provided at a position that overlaps with the proximal end portion of the opening/closing wire 8B when viewed from the width direction W. The hook 81B is provided on the distal end side A1 in relation to the hook 41*f*. The hook 81B is formed to be elastically deformable.

The opening/closing wire 8B is pulled toward the proximal end side A2 by the hook 81B to apply a pulling force to the first arm 211 and the second arm 212 toward the closing side H1 in the opening and closing direction H.

[Action of Clip 2*b*]

Next, the action of the clip 2B will be described with reference to FIGS. 31 to 37.

As shown in FIG. 31, the clip 2B transitions to the closed form Pc when the opening/closing wire 8B pulls the first arm 211 and the second arm 212 toward the closing side H1 in the opening and closing direction H. The opening/closing wire 8B is pulled toward the proximal end side A2 in the longitudinal direction A by the hook 81B provided in the connecting member 4 to transition the clip 2B to the closed form Pc.

Figure 33:
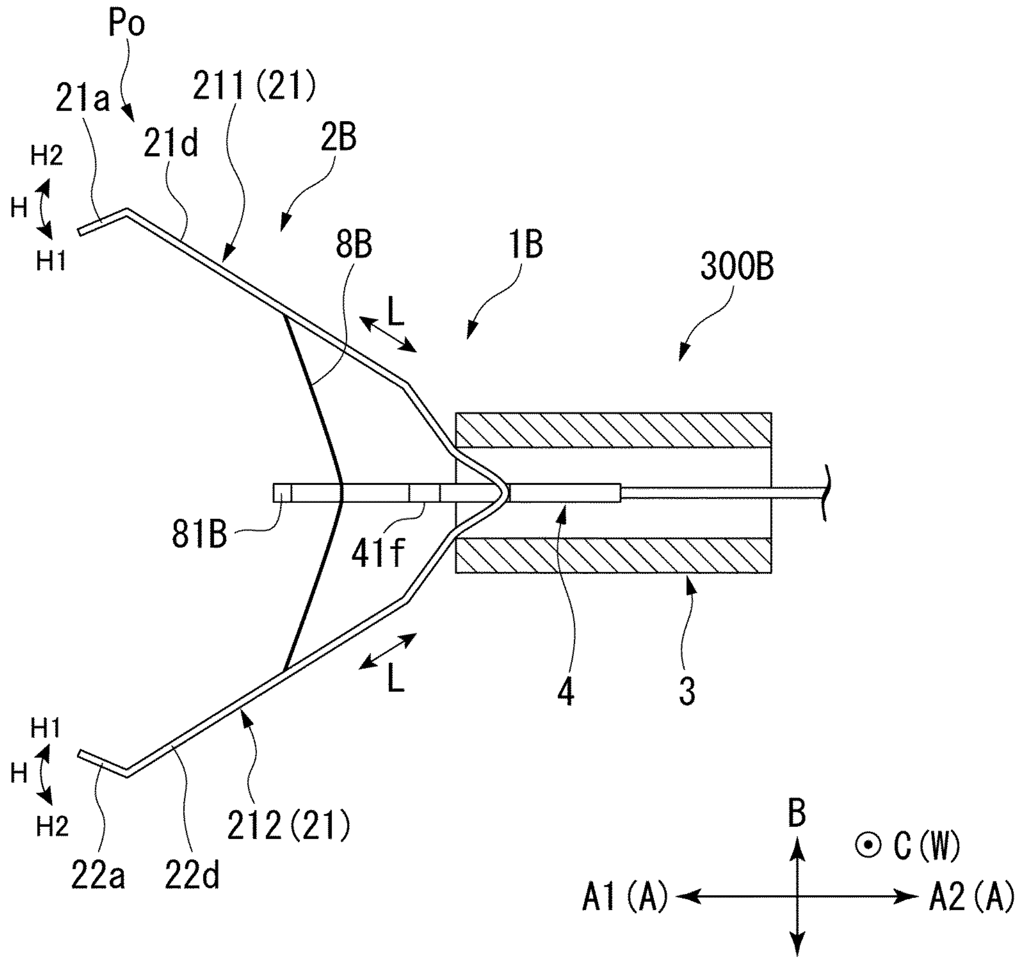
FIG. 33 is a side view showing the clip device in an open form.

FIG. 33 is a side view showing the clip device 300B in the open form Po.

When no force is applied to the arm 21, the clip 2B returns to the open form Po by using the self-expanding force as a restoring force. As shown in FIG. 33, when the opening/closing wire 8B is released from the state where the opening/closing wire is pulled toward the proximal end side A2 in the longitudinal direction A by the hook 81B, the clip 2B transitions to the open form Po. By opening and closing the clip 2B, for example, the mucosa can be grasped.

Figure 34:
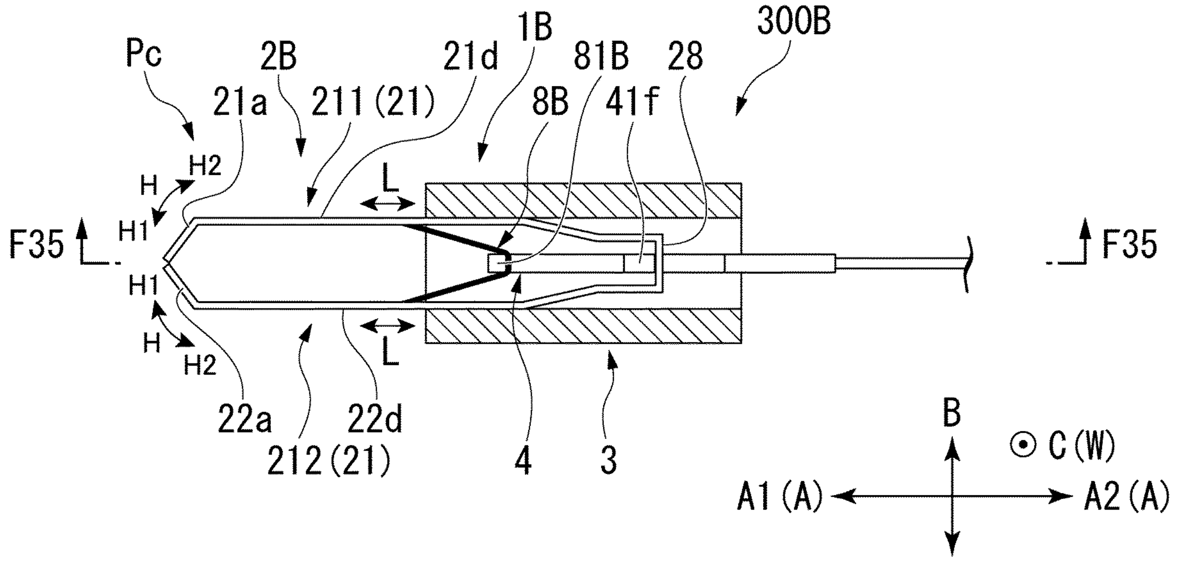
FIG. 34 is a side view showing the clip device in a closed form and showing a clip in a locked state.
Figure 35:
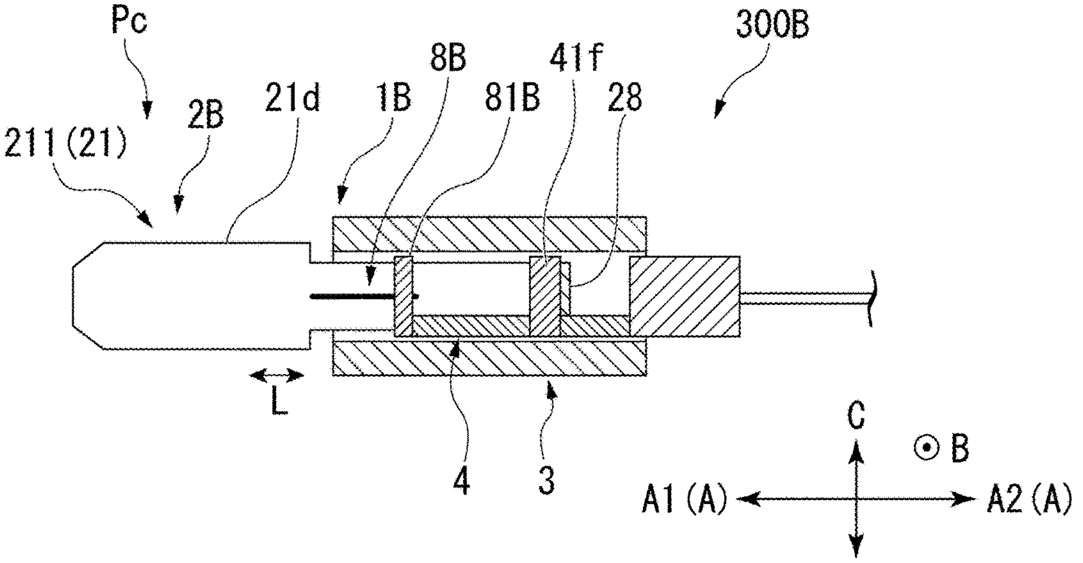
FIG. 35 is a cross-sectional view of the clip device shown in FIG. 34 taken along line F35-F35.

FIG. 34 is a side view showing the clip device 300B in the closed form Pc and showing a state where the clip 2B is locked. FIG. 35 is a cross-sectional view taken along line F35-F35 of the clip device 300B shown in FIG. 34.

When the clip 2B is further pulled toward the proximal end side A2 in the longitudinal direction A from the closed form Pc, the clip 2B transitions to a locked state. The locked state is a state where the transition from the closed form Pc to the open form Po is not possible. When the connecting member 4 is further pulled toward the proximal end side A2 in the longitudinal direction A in the closed form Pc, the proximal end of the clip 2B engages with (contacts) the hook 41*f* of the connecting member 4. When the clip 2 is pulled toward the proximal end side A2 in the longitudinal direction A by the hook 41*f*, the engagement portion 25 formed in the clip 2B engages with the fastening member 32 formed in the pressing member 3 so that the clip 2B transitions to a locked state.

Figure 36:
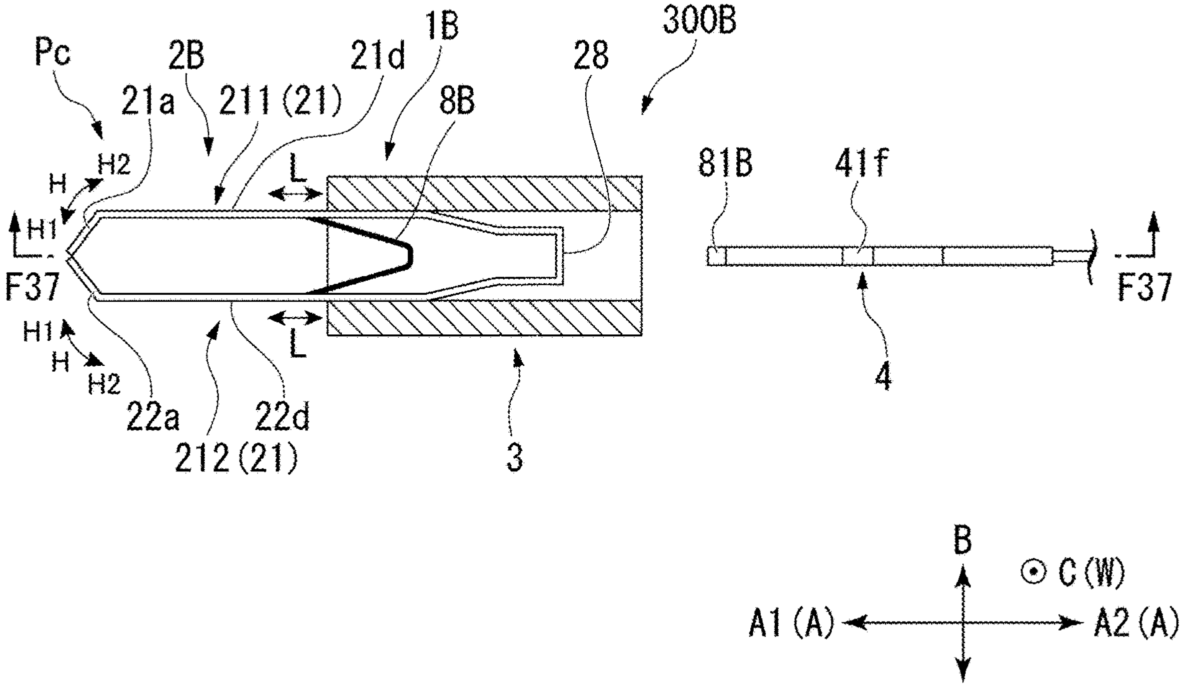
FIG. 36 is a diagram showing the clip device from which the clip is separated.
Figure 37:
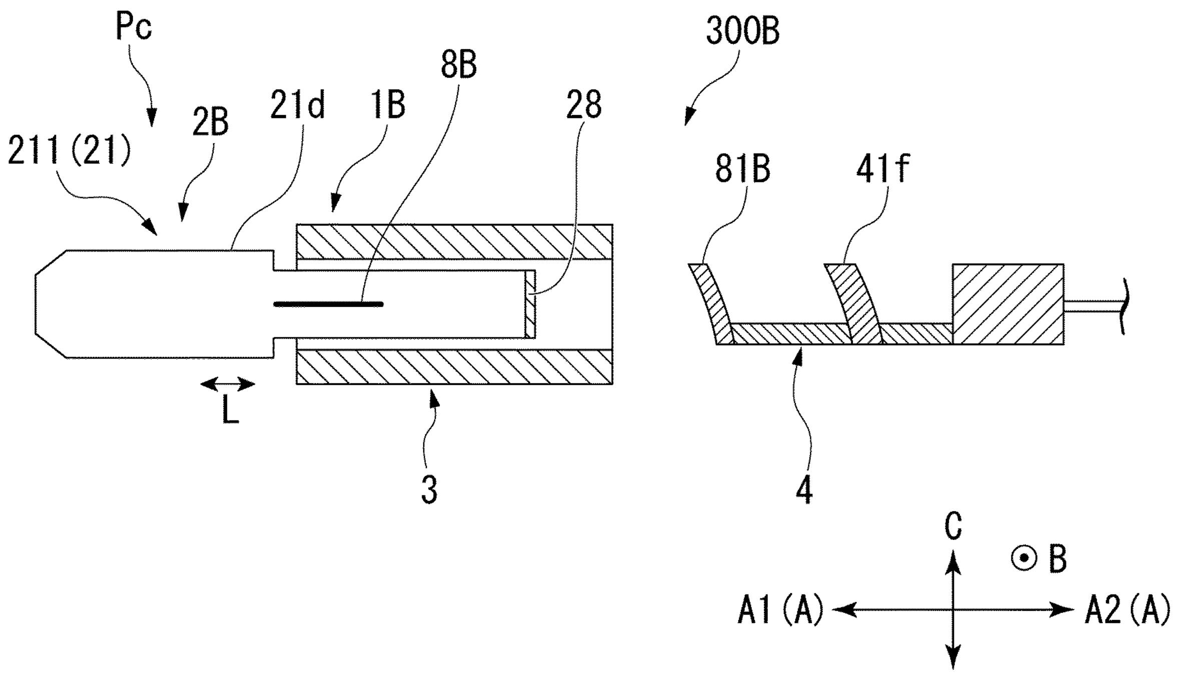
FIG. 37 is a cross-sectional view of the clip device shown in FIG. 36 taken along line F37-F37.

FIG. 36 is a diagram showing the clip device 300B from which the clip 2B is separated. FIG. 37 is a cross-sectional view taken along line F37-F37 of the clip device 300B shown in FIG. 36.

When the connecting member 4 is further pulled toward the proximal end side A2 in the longitudinal direction A from the state where the clip 2B is locked, the clip 2B is separated from the connecting member 4. In this embodiment, since the hook 41*f* and the hook 81F are formed to be elastically deformable, when the connecting member 4 is pulled toward the proximal end side A2 in the longitudinal direction A with a force of a predetermined magnitude or more, the engagement between the hook 41*f* and the proximal end of the clip 2B is released, and the engagement between the hook 81B and the opening/closing wire 8B is released.

[Action of Opening/Closing Wire 8B]

Since the opening/closing wire 8B is provided, the clip device 300B can transition to the insertion form Pi while a clearance is formed between the first and second arms 211 and 212 and the pressing member 3. Therefore, the first arm 211 and the second arm 212 are pivotable relative to the pressing member 3.

Since the opening/closing wire 8B is a string-shaped member, it is possible to apply a force to the first arm 211 and the second arm 212 while maintaining a state where the first arm 211 and the second arm 212 are pivotable relative to the pressing member 3.

The clip device 300B can transition to the insertion form Pi in a state where a clearance is formed between the proximal end portion 29 of the clip 2B and the hook 41*f*. Therefore, the first arm 211 and the second arm 212 are pivotable about the proximal end portion 29 relative to the pressing member 3.

According to the clip device 300B of this embodiment, since the opening/closing wire 8B is provided, the arm 21 is pivotable relative to the pressing member 3, and the distal end of the arm 21 can be prevented from contacting the inner wall of the treatment tool insertion channel N of the endoscope. Therefore, the clip device 300B has good insertability. Since the insertability of the clip device 300B is good, the user can begin treatment of biological tissue as soon as possible.

First Modified Example

Next, a modified example of the clip device 300B will be described with reference to FIG. 38.

Figure 38:
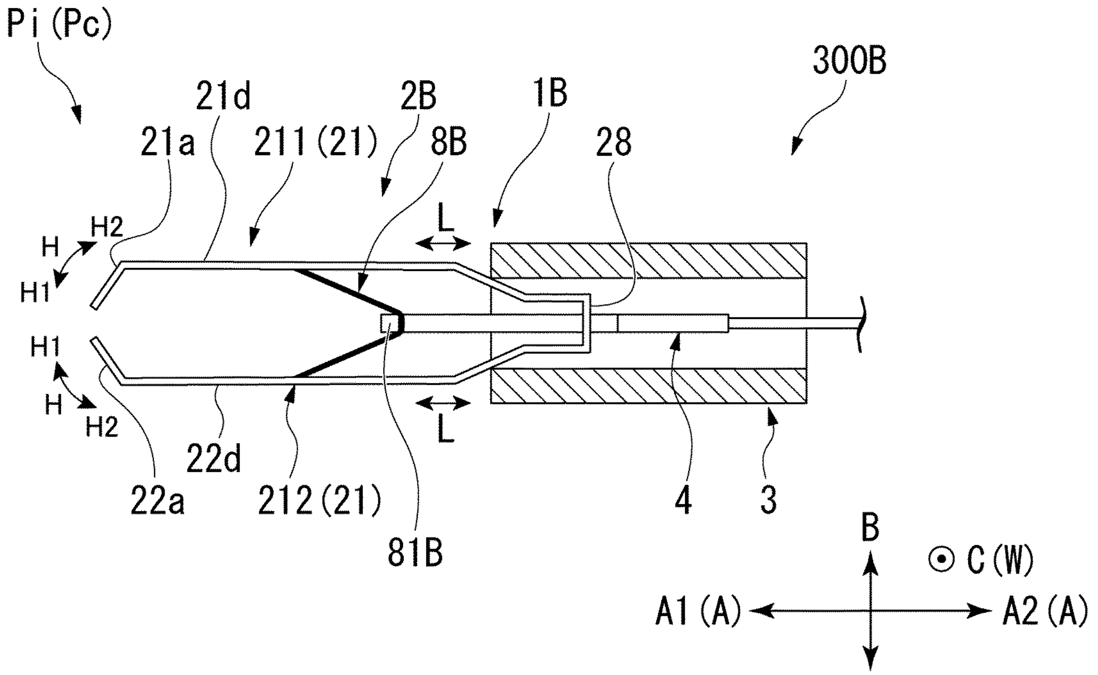
FIG. 38 is a side view showing a modified example of the clip device.

FIG. 38 is a side view showing the modified example of the clip device 300B.

As shown in FIG. 38, the clip device 300B may not have the hook 41*f*. When the hook 41*f* is not provided, the clip 2B is pulled by the connecting member 4 via the opening/closing wire 8B and the hook 81B. Since the hook 41*f* is not formed, the configuration of the clip device 300B can be simplified, and the cost can be further reduced.

Although the second embodiment of the present invention has been described in detail above with reference to the drawings, the specific configuration is not limited to this embodiment, and design changes and the like within the scope of the gist of the present invention are also included. Further, the components shown in the above-described embodiments and the modified examples shown below can be appropriately combined to form a configuration.

Third Embodiment

[Clip Device 300C]

A clip device 300C according to a third embodiment of the present invention will be described with reference to FIGS. 39 to 41. The clip device 300C according to the third embodiment is different from the clip device 300 according to the first embodiment in the configurations of the clip and the like. In the following description, components common to those already described will be indicated by the same reference numerals and a duplicated description will be omitted.

Figure 39:
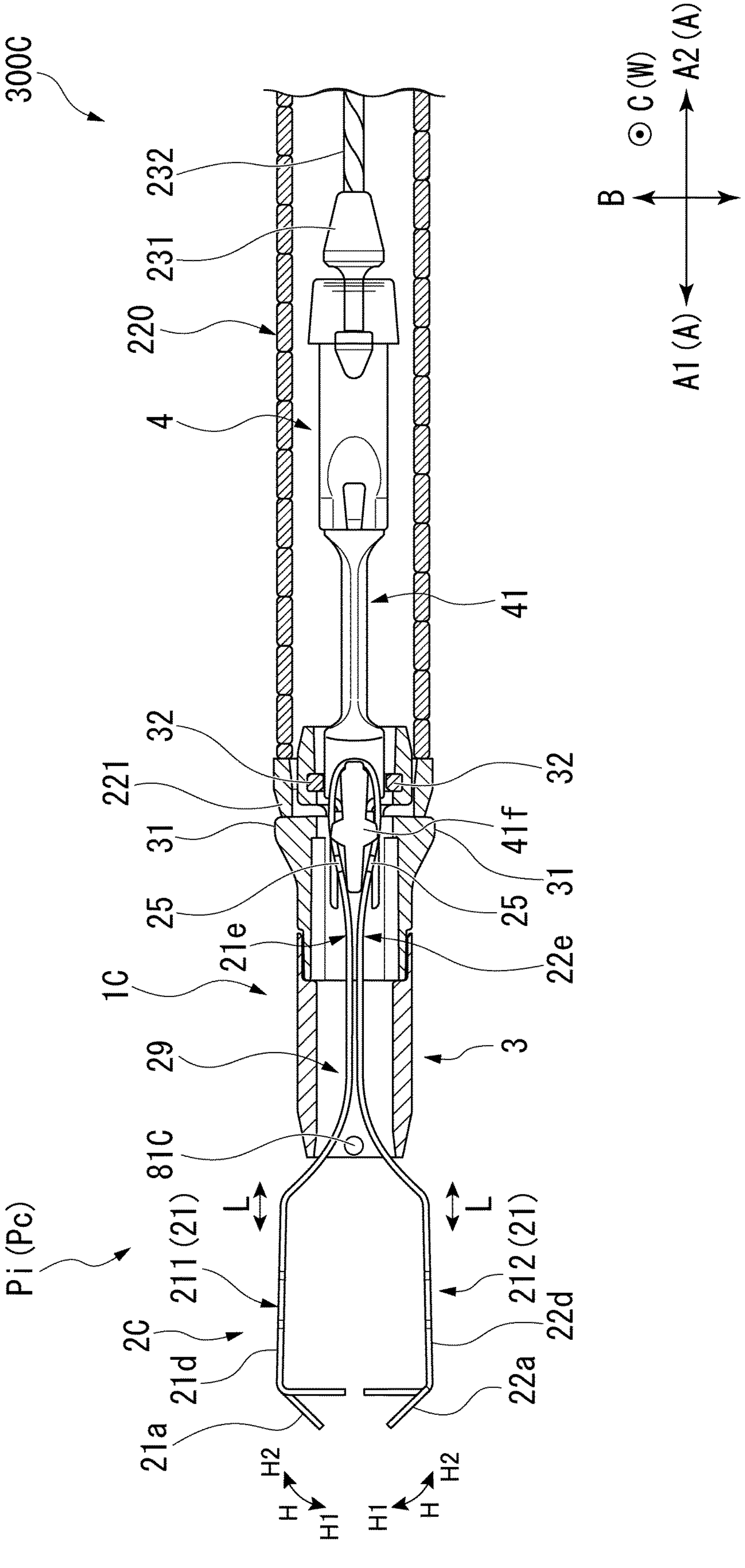
FIG. 39 is a side view showing a clip device according to a third embodiment in a closed form.

FIG. 39 is a side view showing the clip device 300C in the closed form Pc.

The clip device 300C includes the clip introducing device (applicator) 200 and a clip unit 1C. The clip unit 1C is loaded into the clip introducing device 200 as in the clip unit 1. The clip unit 1C is housed in the cartridge 5 as in the clip unit 1.

The clip unit 1C has a clip 2C, the pressing member 3, and the connecting member 4. The clip 2C is supported by the pressing member 3. The clip 2C is connected to the clip introducing device 200 via the connecting member 4.

[Clip 2*c*]

The clip 2C is formed by bending a metal plate material at the center as in the clip 2, and has the first arm 211 and the second arm 212 that are openable and closable. In the insertion form Pi, the clip 2C is provided so as to be pivotable about the proximal end portion 29 of the arm 21 relative to the pressing member 3.

The first arm 211 and the second arm 212 are biased by the connecting portion 28 to be in the closed form Pc. Therefore, the first arm 211 and the second arm 212 maintain the closed form Pc when not receiving an external force.

In the first arm 211 and the second arm 212 in the insertion form Pi, in this embodiment, the distal end 21*r* of the first claw 21*c* and a distal end 22*r* of the second claw 22*c* are spaced apart in the opening and closing direction H. That is, the distal end 21*r* of the first claw 21*c* and the distal end 22*r* of the second claw 22*c* are spaced apart in the opening and closing direction H in the insertion form Pi.

Since the distal end 21*r* of the first claw 21*c* and the distal end 22*r* of the second claw 22*c* are spaced apart in the opening and closing direction H in the insertion form Pi, the first arm 211 is allowed to be shifted toward the closing side in the opening and closing direction H relative to the second arm 212. Therefore, the insertability of the clip device 300C becomes better.

In this embodiment, the pressing member 3 is provided with a pin 81C. The pin 81C is provided at the distal end of the pressing member 3. The pin 81C is a member that extends in the width direction W from the inner wall of the pressing member 3. The pin 81C is a member that transitions the arm 21 to the open form Po.

[Action of Clip 2C]

Next, the action of the clip 2C will be described with reference to FIGS. 39 to 41.

As shown in FIG. 39, the clip 2C maintain the closed form Pc when not receiving an external force. That, the clip 2C is in the insertion form Pi when not receiving an external force. When the clip 2C is in the insertion form Pi, the gap between the first sliding portion 21*e* and the second sliding portion 22*e* in a first direction B is smaller than the width of the pin 81C. When the clip 2C is in the insertion form Pi, the first sliding portion 21*e* and the second sliding portion 22*e* extend in the longitudinal direction A. That is, when the clip 2C is in the insertion form Pi, a gap smaller than the width of the pin 81C in the clip 2C extends in the longitudinal direction A.

Figure 40:
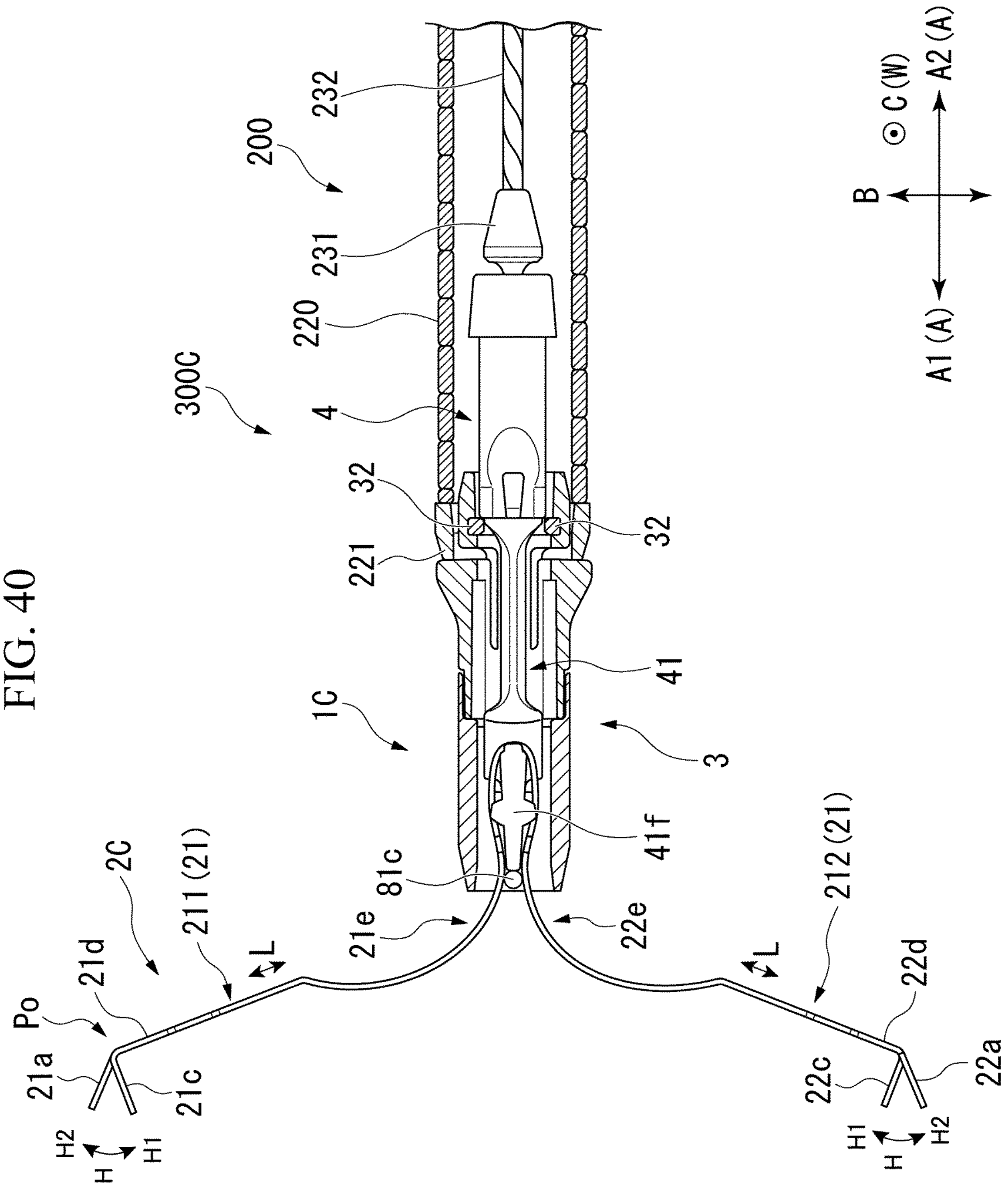
FIG. 40 is a side view showing the clip device in an open form.

FIG. 40 is a side view showing the clip device 300C in the open form Po.

The clip 2C receives a force from the pin 81C provided on the pressing member 3 toward the opening side H2 in the opening and closing direction H to transition from the closed form Pc to the open form Po. The clip 2C is moved toward the distal end side A1 in the longitudinal direction A so that the pin 81C is disposed between the first sliding portion 21*e* of the first arm 211 and the second sliding portion 22*e* of the second arm 212. The clip 2C is further moved toward the distal end side A1 in the longitudinal direction A so that the pin 81C applies a force to the first sliding portion 21*e* and the second sliding portion 22*e* toward the opening side H2 in the opening and closing direction H. Therefore, the first arm 211 and the second arm 212 transition to the open form Po by receiving a force from the pin 81C on the opening side H2 as shown in FIG. 40. By opening and closing the clip 2B, for example, the mucosa can be grasped.

Figure 41:
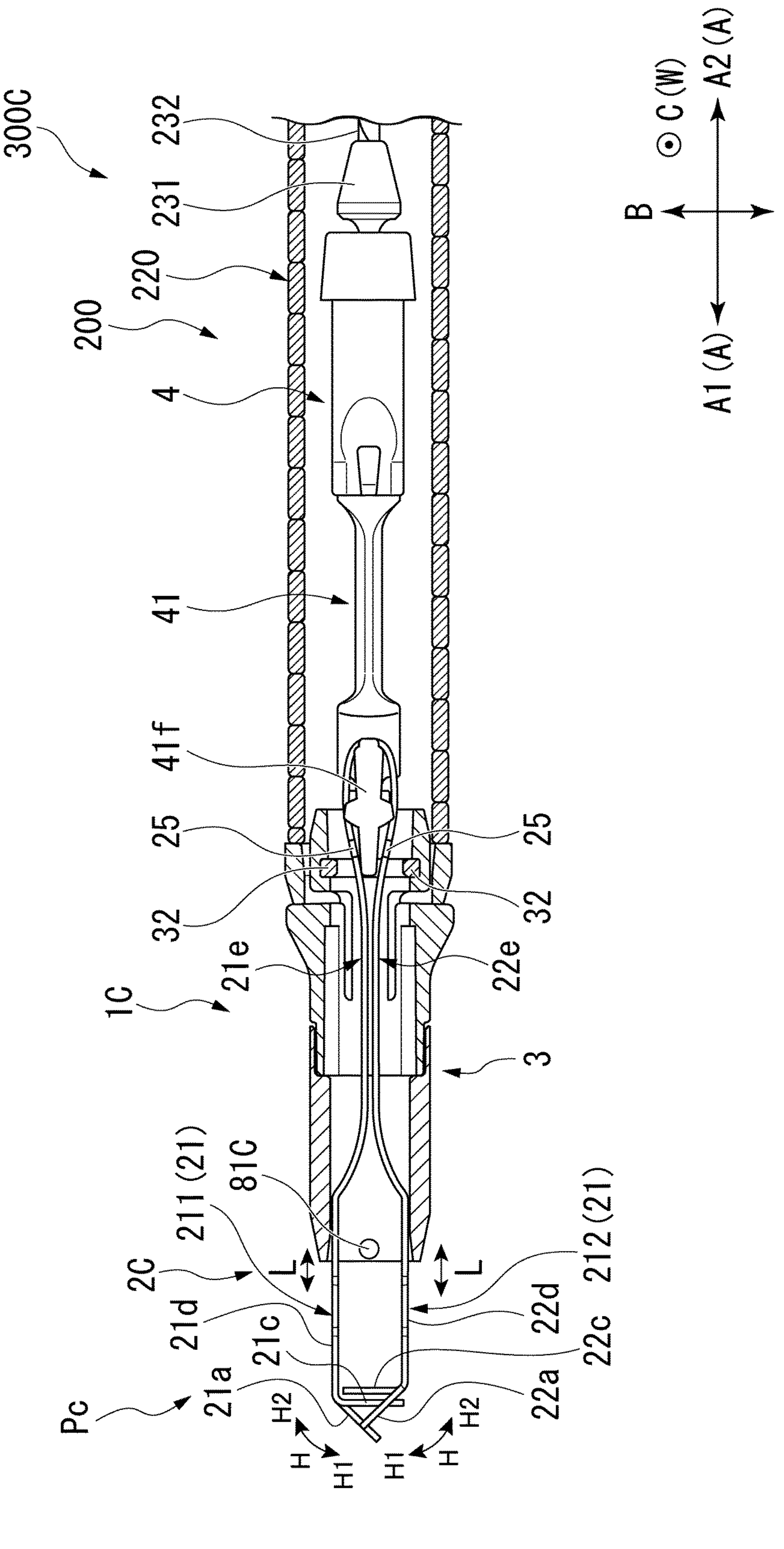
FIG. 41 is a side view showing the clip device in a closed form and showing a clip in a locked state.

FIG. 41 is a side view showing the clip device 300C in the closed form Pc and shows a state where the clip 2C is locked.

The clip 2C is further pulled toward the proximal end side A2 in the longitudinal direction A in the closed form Pc to transition to a locked state. The locked state is a state where the transition from the closed form Pc to the open form Po is not possible. When the connecting member 4 is further pulled toward the proximal end side A2 in the longitudinal direction A in the closed form Pc, the engagement portion 25 formed in the clip 2C engages with the fastening member 32 formed in the pressing member 3 so that the clip 2C transitions to a locked state. When the clip 2C is in the locked state, the first claw 21*c* and the second claw 22*c* are completely closed. That is, in the locked state, there is no gap between the distal end 21*r* of the first claw 21*c* and the distal end 22*r* of the second claw 22*c* in the opening and closing direction H.

Since the first arm 211 and the second arm 212 are biased to be in the closed form Pc, the clip device 300C can transition to the insertion form Pi while a clearance is formed between the first and second arms 211 and 212 and the pressing member 3. Therefore, the first arm 211 and the second arm 212 are pivotable relative to the pressing member 3.

According to the clip device 300C of this embodiment, since the first arm 211 and the second arm 212 are biased to be in the closed form Pc, the arm 21 is pivotable relative to the pressing member 3, and the distal end of the arm 21 can be prevented from contacting the inner wall of the treatment tool insertion channel N of the endoscope. Therefore, the clip device 300C has good insertability. Since the insertability of the clip device 300C is good, the user can begin treatment of biological tissue as soon as possible.

Although the third embodiment of the present invention has been described in detail above with reference to the drawings, the specific configuration is not limited to this embodiment, and design changes and the like within the scope of the gist of the present invention are also included. Further, the components shown in the above-described embodiments and the modified examples shown below can be appropriately combined to form a configuration.

Fourth Embodiment

[Clip Device 300*d*]

A clip device 300D according to a fourth embodiment of the present invention will be described with reference to FIGS. 42 to 49. The clip device 300D according to the fourth embodiment is different from the clip device 300 according to the first embodiment in the configurations of the clip and the like. In the following description, components common to those already described will be indicated by the same reference numerals and duplicated description will be omitted.

Figure 42:
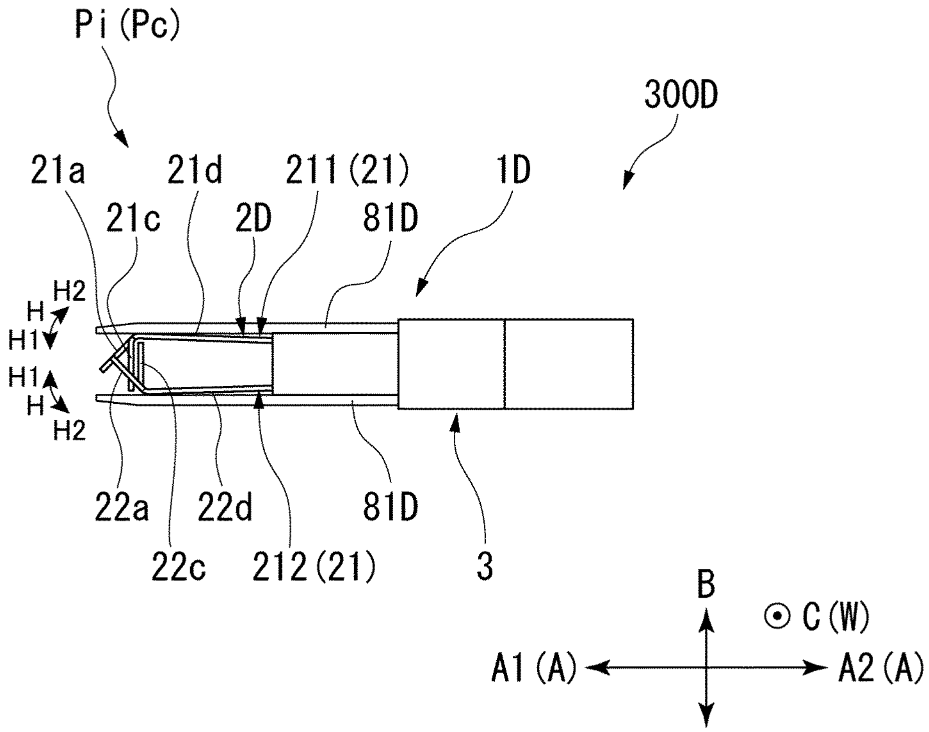
FIG. 42 is a side view showing a clip device according to a fourth embodiment in a closed form when viewed from a width direction.
Figure 43:
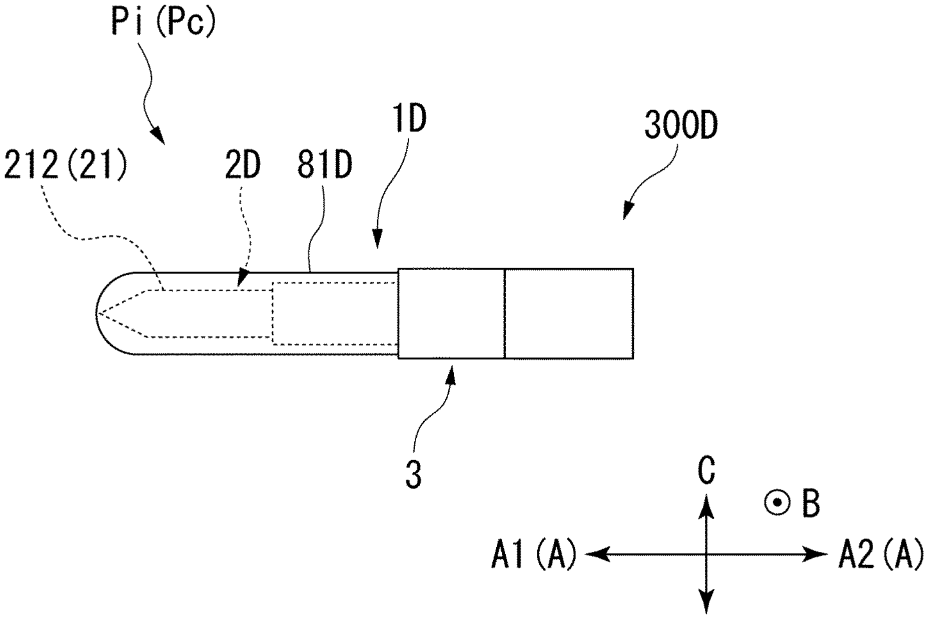
FIG. 43 is a side view showing the clip device in a closed form when viewed from an opening and closing direction.

FIG. 42 is a side view showing the clip device 300D in the closed form Pc when viewed from the width direction W. FIG. 43 is a side view showing the clip device 300D in the closed form Pc when viewed from the opening and closing direction H.

The clip device 300D includes the clip introducing device (applicator) 200 and a clip unit 1D. The clip unit 1D is loaded into the clip introducing device 200 as in the clip unit 1. The clip unit 1D is housed in the cartridge 5 as in the clip unit 1.

The clip unit 1D has a clip 2D, the pressing member 3, and the connecting member 4. The clip 2D is supported by the pressing member 3. The clip 2D is connected to the clip introducing device 200 via the connecting member 4.

[Clip 2*d*]

The clip 2D is formed by bending a metal plate material at the center as in the clip 2, and has the first arm 211 and the second arm 212 that are openable and closable. The clip 2D is covered by a cover 81D in the insertion form Pi.

The cover 81D covers the clip 2D in the insertion form Pi from the opening side in the opening and closing direction H. The cover 81D is provided with the clip 2D in the insertion form Pi interposed therebetween in the opening and closing direction H. The cover 81D covers the first anchor 21*a* and the second anchor 22*a* from the opening side in the opening and closing direction H. Furthermore, the position where the cover 81D covers the clip 2D is not limited. For example, the cover 81D may be formed to cover the clip 2D from the width direction W.

In this embodiment, the cover 81D is provided at the distal end of the pressing member 3. The cover 81D extends to the distal end 21*p* of the first anchor 21*a* and the distal end 22*p* of the second anchor 22*a*. Furthermore, the installation position of the cover 81D is not limited. For example, the cover 81D may be provided in the first arm body 21*d*.

The cover 81D has a plate shape in which the opening and closing direction H is the plate thickness direction. The cover 81D is formed to be elastically deformable. Therefore, when the first arm 211 and the second arm 212 transition from the closed form Pc to the open form Po, the cover 81D is pressed toward the opening side H2 in the opening and closing direction H by the first arm 211 and the second arm 212, and the cover 81D opens toward the opening side H2. Furthermore, the configuration of the cover 81D is not limited. For example, the cover 81D may be rotatably attached to the pressing member 3.

[Action of Clip 2*d*]

Next, the action of the clip 2D will be described with reference to FIGS. 42 to 45.

Figure 44:
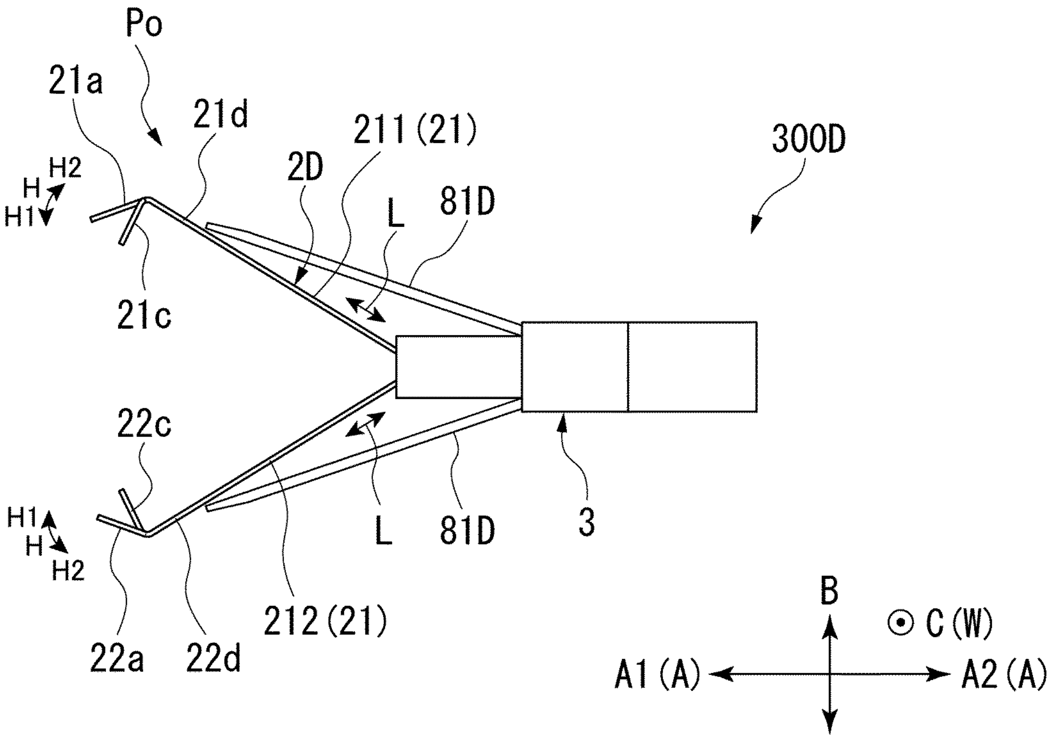
FIG. 44 is a side view showing the clip device in an open form.

FIG. 44 is a side view showing the clip device 300D in the open form Po.

When the clip 2D is in the open form Po, the cover 81D is pressed toward the opening side H2 in the opening and closing direction H by the first arm 211 and the second arm 212, and the cover 81D opens toward the opening side H2. Further, the first arm 211 and the second arm 212 protrude toward the distal end relative to the pressing member 3 in the open form Po compared to the closed form Pc. Therefore, the cover 81D is disposed on the proximal end side A2 in relation to the distal ends of the first arm 211 and the second arm 212 in the open form Po. That is, the first anchor 21*a*, the first claw 21*c*, the second anchor 22*a*, and the second claw 22*c* are not covered from the opening and closing direction H by the cover 81D in the open form Po. Therefore, the clip 2D can grasp, for example the mucosa.

Figure 45:
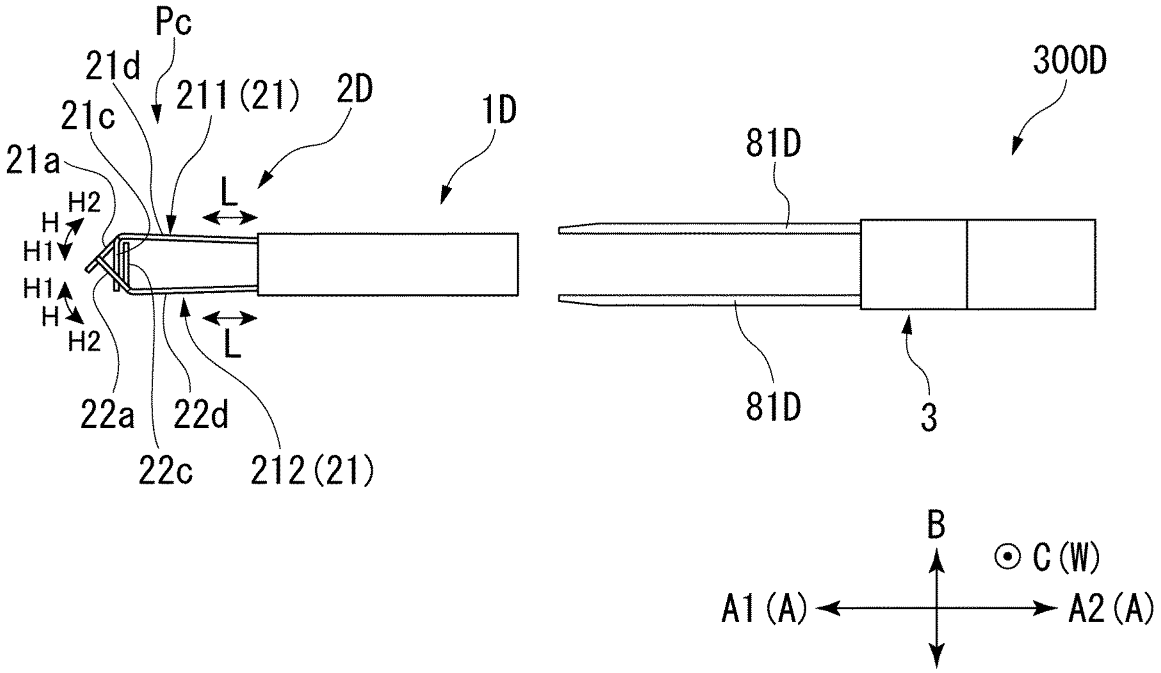
FIG. 45 is a diagram showing the clip device from which the clip is separated.

FIG. 45 is a diagram showing the clip device 300D from which the clip 2D is separated.

As shown in FIG. 45, the clip 2D is provided so as to be separable from the clip device 300D. At this time, since the cover 81D is provided on the pressing member 3, the cover is separated from the clip 2D.

According to the clip device 300D of this embodiment, since the first arm 211 and the second arm 212 are covered by the cover 81D, it is possible to prevent the distal ends of the first anchor 21*a* and the second anchor 22*a* from contacting the treatment tool insertion channel N of the endoscope when the clip device 300D contacts the treatment tool insertion channel N of the endoscope. Therefore, the clip device 300D has good insertability.

Second Modified Example

Next, a modified example of the clip device 300D will be described with reference to FIGS. 46 to 49.

Figure 46:
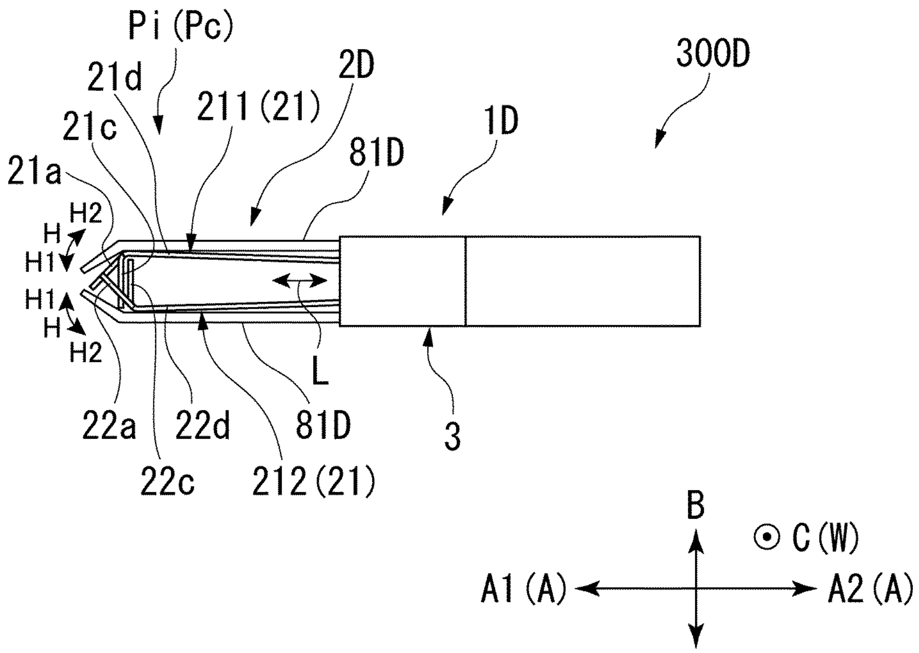
FIG. 46 is a side view showing a clip device of a modified example in a closed form when viewed from a width direction.
Figure 47:
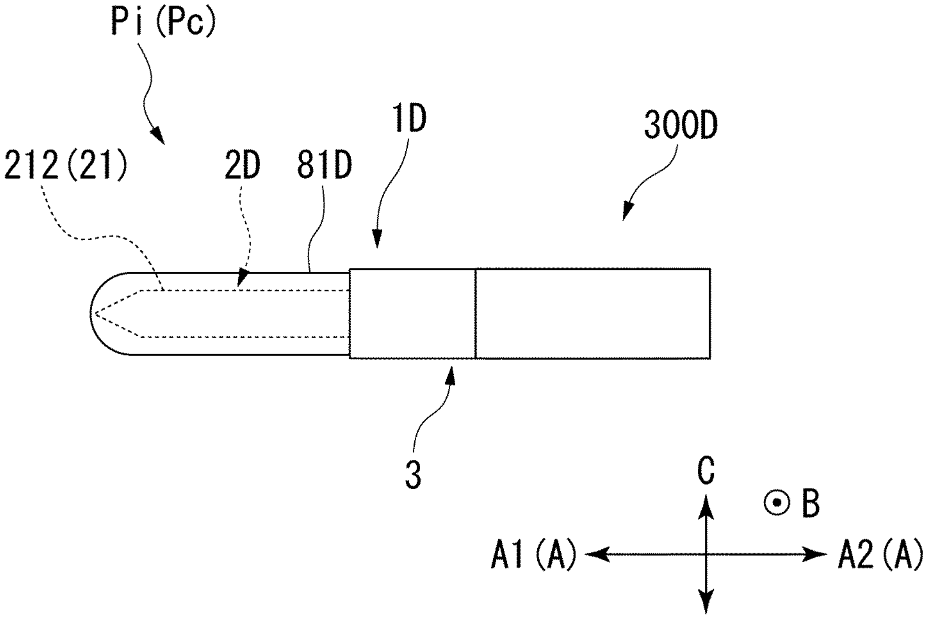
FIG. 47 is a side view showing the clip device in a closed form when viewed from an opening and closing direction.
Figure 48:
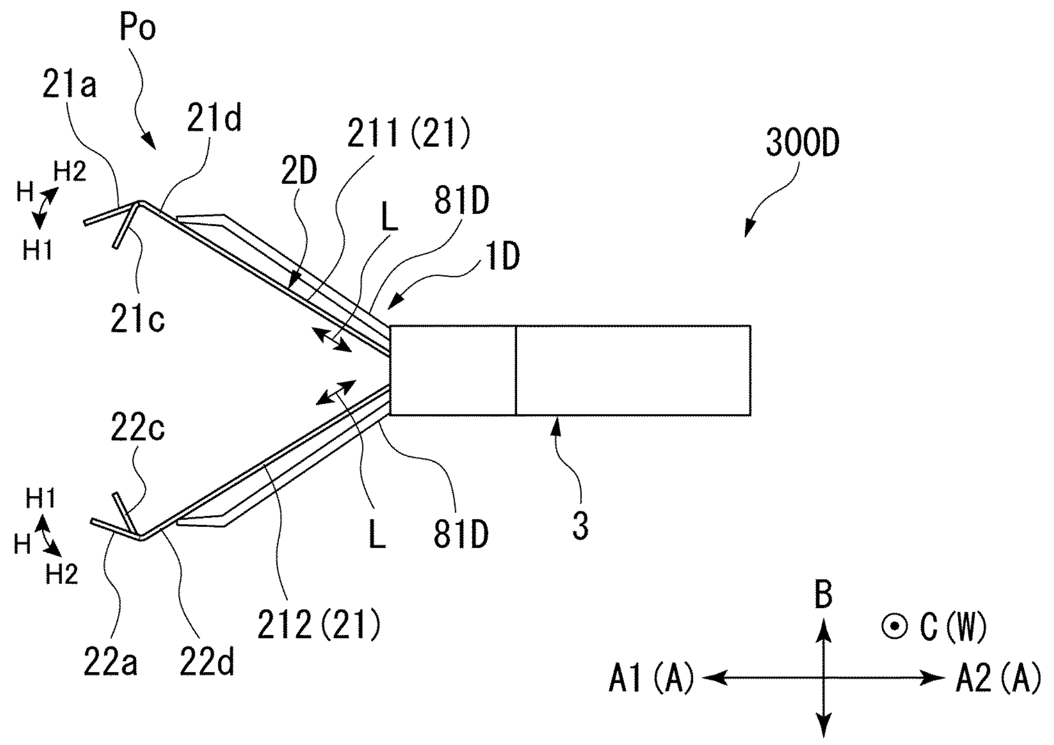
FIG. 48 is a side view showing the clip device in an open form.

FIG. 46 is a side view showing the clip device 300D of the modified example in the closed form Pc when viewed from the width direction W. FIG. 47 is a side view showing the clip device 300D of the modified example in the closed form Pc when viewed from the opening and closing direction H. FIG. 48 is a side view showing the clip device 300D of the modified example in the open form Po.

The shape of the cover 81D provided in the clip device 300D is not limited. As shown in FIG. 46, the tip of the cover 81D may be bent toward the closing side H1 in the opening and closing direction H. Since the distal end of the cover 81D is bent, the cover 81D can cover the distal ends of the first arm 211 and the second arm 212 even when the first arm 211 and the second arm 212 are misaligned with respect to the pressing member 3.

Figure 49:
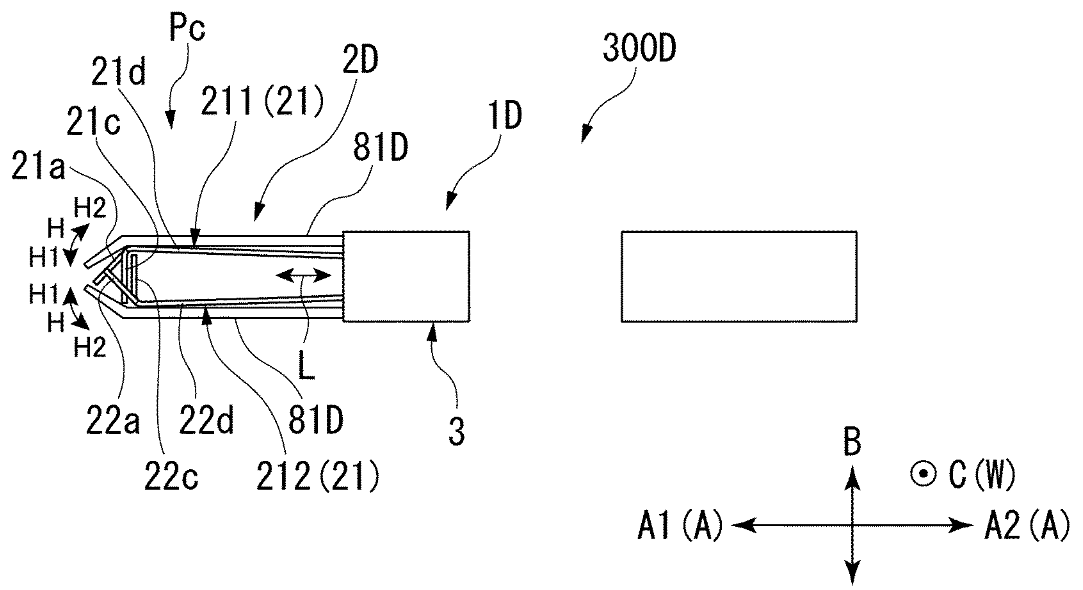
FIG. 49 is a side view showing the clip device from which the clip is separated.

FIG. 49 is a diagram showing the modified example of the clip device 300D from which the clip 2D is separated.

As shown in FIG. 49, the cover 81D may be provided so as to be separable from the clip device 300D while covering the clip 2D when the clip 2D is separated from the clip device 300D. In this case, the cover 81D needs to be made of a material that will not cause any problem if left inside the body.

Although the fourth embodiment of the present invention has been described in detail above with reference to the drawings, the specific configuration is not limited to this embodiment, and design changes and the like within the scope of the gist of the present invention are also included. Further, the components shown in the above-described embodiments and the modified examples shown below can be appropriately combined to form a configuration.

What is claimed is:

1. A clip device comprising:

a clip which has an arm configured to be openable and closable in an opening and closing direction; and a holder which supports the clip and extends in a first longitudinal direction along a first longitudinal axis, wherein;

the arm is configured to pivot in an insertion form in which the arm is closed to be insertable through a channel of an endoscope, about a fulcrum raised portion relative to the holder, and has an arm body and a claw which extends from the arm body toward a closing side in the opening and closing direction;

the fulcrum raised portion is provided at a proximal end portion of the arm body so as to protrude toward an opening side in the opening and closing direction; and the fulcrum raised portion is formed by bending the arm body toward the opening side in the opening and closing direction.

2. The clip device according to claim 1, wherein the arm body extends in a second longitudinal direction along a second longitudinal axis, and wherein in the insertion form, the arm is configured to pivot relative to the holder by transitioning between a straight state where the first longitudinal direction and the second longitudinal direction substantially coincide with each other and a bent state where the first longitudinal direction and the second longitudinal direction intersect with each other.

3. The clip device according to claim 2, wherein the fulcrum raised portion is disposed inside the holder in the insertion form, and in the bent state, the fulcrum raised portion is located on a distal end side in relation to a position relative to the holder in the straight state.

4. The clip device according to claim 1, wherein the fulcrum raised portion comes into contact with the inside of the holder in the insertion form.

5. The clip device according to claim 1, wherein two of the fulcrum raised portions are provided with the proximal end portion of the arm interposed therebetween in the opening and closing direction.

6. The clip device according to claim 5, wherein the arm is able to transition between an open form and a closed form including the insertion form, and wherein the fulcrum raised portion is disposed from the outside to the inside of the holder to transition from the open form to the closed form.

7. The clip device according to claim 1, further comprising:

a wire which is connected to the arm and is able to pull the arm toward a closing side in the opening and closing direction, wherein the arm is able to transition to the insertion form by being pulled toward the closing side in the opening and closing direction by the wire.

8. The clip device according to claim 7, wherein the arm has an arm body which extends in a second longitudinal direction along a second longitudinal axis and a claw which extends from the arm body toward a closing side in the opening and closing direction, and wherein the wire is connected to the arm body.

9. The clip device according to claim 7, wherein the wire is able to pull the arm toward a closing side in the opening and closing direction by being pulled toward a proximal end side in the first longitudinal direction.

10. The clip device according to claim 1, wherein the arm has a pair of arm bodies which extend in a second longitudinal direction along a second longitudinal axis and a pair of claws which extend from the pair of arm bodies toward a closing side in the opening and closing direction, and wherein distal ends of the pair of claws are spaced apart in the opening and closing direction in the insertion form.

11. The clip device according to claim 1, wherein the arm has an arm body which extends in a second longitudinal direction along a second longitudinal axis, a claw which is provided at a distal end of the arm body and extends toward a closing side in the opening and closing direction, and an anchor which is provided at a distal end of the arm body and extends toward an opening side in relation to the claw in the opening and closing direction.

12. The clip device according to claim 1, wherein the arm has a gripping portion and an elastically deformable curved portion, and wherein the curved portion is elastically deformable by receiving an external force from the holder.

13. The clip device according to claim 1, wherein the clip device is used while being connected to an applicator.

14. The clip device according to claim 13, wherein the clip device is housed in a cartridge, and wherein the clip device is able to be loaded into the applicator by inserting the applicator into the cartridge.

15. A clip device comprising:

a clip which has an arm configured to be openable and closable in an opening and closing direction; and a holder which supports the clip and extends in a first longitudinal direction along a first longitudinal axis, wherein:

the arm is configured to pivot in an insertion form in which the arm is closed to be insertable through a channel of an endoscope, about a fulcrum raised portion relative to the holder, and has an arm body and a claw which extends from the arm body toward a closing side in the opening and closing direction;

the fulcrum raised portion is provided at a proximal end portion of the arm body so as to protrude toward an opening side in the opening and closing direction; and the fulcrum raised portion is formed by extruding the arm body toward the opening side in the opening and closing direction.

16. The clip device according to claim 15, wherein the arm body extends in a second longitudinal direction along a second longitudinal axis, and wherein in the insertion form, the arm is configured to pivot relative to the holder by transitioning between a straight state where the first longitudinal direction and the second longitudinal direction substantially coincide with each other and a bent state where the first longitudinal direction and the second longitudinal direction intersect with each other.

17. The clip device according to claim 16, wherein the fulcrum raised portion is disposed inside the holder in the insertion form, and in the bent state, the fulcrum raised portion is located on a distal end side in relation to a position relative to the holder in the straight state.

18. The clip device according to claim 15, wherein the fulcrum raised portion comes into contact with the inside of the holder in the insertion form.

19. The clip device according to claim 15, wherein two of the fulcrum raised portions are provided with the proximal end portion of the arm interposed therebetween in the opening and closing direction.

20. The clip device according to claim 19, wherein the arm is able to transition between an open form and a closed form including the insertion form, and wherein the fulcrum raised portion is disposed from the outside to the inside of the holder to transition from the open form to the closed form.

* * * * *